United States Patent
Cho et al.

(10) Patent No.: US 7,438,686 B2
(45) Date of Patent: Oct. 21, 2008

(54) APPARATUS AND METHOD FOR MONITORING FOR DISORDERED BREATHING

(75) Inventors: Yong K Cho, Maple Grove, MN (US); Abed E. Lawabni, Minneapolis, MN (US); Todd J Sheldon, North Oaks, MN (US); H T Markowitz, Roseville, MN (US); Sameh Sowelam, Maple Grove, MN (US); Raylene Pitschneider, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 517 days.

(21) Appl. No.: 10/419,404

(22) Filed: Apr. 21, 2003

(65) Prior Publication Data

US 2005/0119711 A1    Jun. 2, 2005

Related U.S. Application Data

(60) Provisional application No. 60/439,409, filed on Jan. 10, 2003.

(51) Int. Cl.
*A61B 5/0205* (2006.01)

(52) U.S. Cl. .................. 600/484; 600/483; 600/529

(58) Field of Classification Search .............. 607/42, 607/17, 19–20, 24–25; 600/529, 483–484
See application file for complete search history.

(56) References Cited

U.S. PATENT DOCUMENTS

| | | | |
|---|---|---|---|
| 4,428,378 A | 1/1984 | Anderson et al. | |
| 4,475,559 A * | 10/1984 | Horn ........................ | 600/529 |
| 4,869,251 A | 9/1989 | Lekholm et al. | |
| 4,896,068 A | 1/1990 | Nilsson | |
| 4,901,725 A | 2/1990 | Nappholz et al. | |
| 5,052,388 A | 10/1991 | Sivula et al. | |
| 5,117,824 A | 6/1992 | Keimel et al. | |
| 5,174,287 A | 12/1992 | Kallok et al. | |
| 5,233,984 A | 8/1993 | Thompson | |
| 5,275,159 A * | 1/1994 | Griebel ........................ | 600/324 |
| 5,485,851 A | 1/1996 | Erickson | |
| 5,507,785 A | 4/1996 | Deno | |
| 5,540,733 A | 7/1996 | Testerman et al. | |
| 5,562,712 A | 10/1996 | Steinhaus et al. | |
| 5,630,834 A | 5/1997 | Bardy | |
| 5,797,852 A * | 8/1998 | Karakasoglu et al. ........ | 600/529 |

(Continued)

FOREIGN PATENT DOCUMENTS

WO    WO 03/092493 A2    11/2003

OTHER PUBLICATIONS

Hilton et al., "Evaluation of Frequency and Time-Frequency Spectral Analysis of Heart Rate Variability as a Diagnostic Marker of the Sleep Apnea Syndrome", *Medical and Biological Engineering & Computing*, 1999; 37:760-769.

*Primary Examiner*—Carl H. Layno
*Assistant Examiner*—Deborah Malamud
(74) *Attorney, Agent, or Firm*—Daniel G. Chapik

(57) ABSTRACT

The present invention relates to a device and method for monitoring for sleep disordered breathing or other types of disordered breathing such as Cheyne-Stokes breathing. More specifically, a device and method for detecting disordered breathing is provided that monitors a physiological parameter, which becomes cyclical due to apnea-hyperpnea (or arousal) alternation and provides the basis for the determination of a number of breathing disorder metrics.

18 Claims, 13 Drawing Sheets

U.S. PATENT DOCUMENTS

| | | |
|---|---|---|
| 5,814,087 A | 9/1998 | Renirie |
| 5,987,352 A | 11/1999 | Klein et al. |
| 6,091,973 A * | 7/2000 | Colla et al. ................. 600/324 |
| 6,126,611 A | 10/2000 | Bourgeois et al. |
| 6,132,384 A | 10/2000 | Christopherson et al. |
| 6,161,041 A | 12/2000 | Stoop et al. |
| 6,208,897 B1 | 3/2001 | Jorgenson et al. .............. 607/5 |
| 6,251,126 B1 | 6/2001 | Ottenhoff et al. |
| 6,334,071 B1 | 12/2001 | Lu |
| 6,375,621 B1 * | 4/2002 | Sullivan ..................... 600/484 |
| 6,574,507 B1 * | 6/2003 | Bonnet ........................ 607/20 |
| 6,641,542 B2 * | 11/2003 | Cho et al. ................... 600/529 |
| 6,752,765 B1 * | 6/2004 | Jensen et al. ................ 600/536 |
| 6,881,192 B1 * | 4/2005 | Park .......................... 600/529 |
| 2001/0018557 A1 * | 8/2001 | Lynn et al. .................. 600/324 |
| 2002/0095076 A1 * | 7/2002 | Krausman et al. ........... 600/323 |
| 2002/0169384 A1 | 11/2002 | Kowallik et al. ............ 600/529 |
| 2003/0153953 A1 * | 8/2003 | Park et al. .................... 607/17 |

* cited by examiner

APPARATUS AND METHOD FOR MONITORING FOR DISORDERED BREATHING

CROSS REFERENCE TO RELATED APPLICATION

This patent disclosure claims the benefit of provisional U.S. patent application Ser. No. 60/439,409 filed 10 Jan. 2003.

FIELD OF THE INVENTION

The present invention relates to a device and method for monitoring for sleep disordered breathing or other types of disordered breathing such as Cheyne-Stokes breathing. More specifically, a device and method for detecting disordered breathing is provided that monitors a physiological parameter, which becomes cyclical due to apnea-hyperpnea (or arousal) alternation and provides the basis for the determination of a number of breathing disorder metrics.

BACKGROUND OF THE INVENTION

Sleep apnea, the temporary cessation of respiratory airflow during sleep, is generally considered a medical syndrome that occurs in at least three recognized forms. The first is central sleep apnea, associated with the failure of the central nervous system to automatically initiate and control respiration. The second is obstructive sleep apnea, associated with an obstruction of the airways due to their collapse. A third, mixed form may include a central nervous system failure to drive ventilatory effort combined with an obstructive apnea. Daytime sleepiness and associated cardiovascular diseases significantly impair patient lifestyle and increase morbidity risk. Various approaches have been taken to detect and treat sleep apnea.

A standard diagnostic approach for sleep apnea includes polysomnography, which requires the patient to stay overnight in a hospital for observation, in addition to medical history and screening questionnaires. Polysomnography involves monitoring of multiple parameters including electroencephalography, electromyography, electrocardiography, oximetry, airflow, respiratory effort, snoring, body position and blood pressure. This intensive and costly approach is not practical for screening large numbers of patients, yet the prevalence of undiagnosed sleep apnea in the U.S. is thought to be in the millions with on the order of 2% of middle-aged women and 4% of middle-aged men having sleep apnea syndrome. See Young T. et al., "The occurrence of sleep-disordered breathing among middle-aged adults," *New England J. Med.* 1993;328:1230-1235. An apnea-hypopnea index (AHI) is used by physicians to gauge the severity of sleep apnea. AHI is the number of apnea-hypopnea episodes occurring per hour during a monitored period. It is estimated that 9% of women and 24% of men have an AHI greater than 5, indicating at least a mild to moderate sleep apnea condition.

A method for screening and diagnosing sleep apnea that is less costly and less stressful to the patient than polysomnography is needed, therefore, in order to reach the large number of patients having undiagnosed sleep apnea. A method of identifying a breathing parameter that is characteristic of the breathing status of a sleeping individual and measuring the derivative trend with respect to time of one variable of state of the cardiovascular system, which variable recurrently changes with the respiration is generally disclosed in U.S. Pat. Application No. 20020169384 to Kowallik et al. A microprocessor system for the simplified diagnosis of sleep apnea, which includes an inexpensive system for the collection and analysis of pulse oximetry values as a function of time during sleep is generally disclosed in U.S. Pat. No. 20020173707 to Lynn et al.

Once diagnosed, a common mode of treatment is application of continuous positive airway pressure (CPAP) to maintain patency of the airways. Continuous positive airway pressure is applied throughout the night and can cause considerable stress to the patient. Alternative therapeutic approaches involve detecting the onset of an apnea episode and then delivering a therapy to either maintain airway patency or counteract autonomic-mediated causes during apnea. For example, electrical stimulation of the hypoglossal nerve or muscles of the upper airways has been proposed or attempted clinically. Reference is made to U.S. Pat. No. 5,540,733 issued to Testerman et al., U.S. Pat. No. 5,174,287 issued to Kallok, and U.S. Pat. No. 6,251,126 issued to Ottenhoff et al., all of which patents are incorporated herein by reference in their entirety.

Detection of sleep apnea for the purposes of triggering the delivery of a sleep apnea therapy may be based on respiratory monitoring. Measuring respiratory effort by monitoring airway pressures is generally disclosed in the above-cited U.S. Pat. No. 5,540,733 issued to Testerman and in U.S. Pat. No. 6,132,384 issued to Christopherson et al. A method for monitoring electrical activity associated with contractions of the diaphragm and the pressure within the thorax and upper airway is generally disclosed in U.S. Pat. No. 5,174,287 issued to Kallok.

Sleep apnea is known to have cardiovascular consequences including changes in cardiac rhythm, hemodynamic fluctuations, and hypertension. Low oxygen levels due to sleep apnea are associated with an increased morbidity due to cardiovascular complications, including heart attack and stroke. Overdrive pacing of the heart upon detection of sleep apnea is proposed in U.S. Pat. No. 6,126,611 issued to Bourgeois et al., incorporated herein by reference in its entirety. However, a high pacing rate may tend to arouse the patient, ending the apnea. Although, the inventors hereof believe that significantly increased nocturnal overdrive pacing (NOP)—relative to a typical mean pacing rate during sleep will not wake a patient.

Heart rate variability and frequency and time domain analysis of the heart rate have also been proposed for detecting apnea. Frequency and time domain analysis of heart rate variability may require sophisticated algorithms that may be performed on a personal computer but may not be suitable for implementation in an implantable device because of the intensive microprocessing time and power required. Cyclical variation of the heart rate in sleep apnea syndrome has been observed as progressive bradycardia, followed by abrupt tachycardia on resumption of breathing. See Guilleminault C. et al., "Cyclical variation of the heart rate in sleep apnoea syndrome: Mechansims and usefulness of 24 h electrocardiography as a screening technique." QT interval changes have also been observed during obstructive sleep apnea syndrome with a progressive prolongation of the QT interval during apnea and an abrupt shortening during the postapnea period. Significant changes in the R-R interval or QT interval were not observed during normal REM sleep. Ambulatory ECG monitoring may be used for monitoring for these electrocardiogram changes, however, external monitoring or therapy delivery devices are generally subject to the limitation of patient compliance.

An improved method is needed for detecting sleep apnea or other disordered breathing patterns that does not require complicated sensors or signal processing and may be readily implemented in an implantable device. The method preferably provides diagnostic or prognostic data that may be used for screening, diagnosing, and monitoring patients for apnea or other breathing disorders such as Cheyne-Stokes breathing and may provide apnea detection for triggering the delivery of a therapy and monitoring for therapy evaluation.

SUMMARY OF THE INVENTION

The present invention addresses the above-described needs by providing an improved method for monitoring for sleep apnea or other breathing disorders, such as Cheyne-Stokes breathing, collectively referred to herein as "disordered breathing," based on a physiological signal that undergoes cyclical variation in association with apnea and hypopnea episodes. The present invention may be implemented in an implantable device using one or more sensors of selected physiological parameters. In a preferred embodiment, methods included in the present invention are implemented in an implantable device having at least one sensor for determining the patient's heart rate. For example, a monitoring method may be implemented in an implantable device having electrodes for sensing ECG or electrogram (EGM) signals from which a heart rate can be determined. Cyclical variations in heart rate are detected and used for recognizing apnea-hypopnea cycles.

In another embodiment, a monitoring method in accordance with the present invention may be implemented in an implantable device equipped with impedance sensing capabilities for measuring thoracic impedance from which minute volume may be derived. Such an implantable medical device may comprise a set of electrodes embedded or disposed around a canister portion of an implantable medical device. For example, such devices may have a set of surface mounted electrodes capable of sensing cardiac electrical activity. Such devices may also have one or more deployable medical electrical leads adapted to sense electrical cardiac activity signals between two or more electrodes. Cyclical changes in minute volume are detected and used for detecting apnea episodes.

In yet another embodiment, a monitoring method is implemented in an implantable device having both EGM sensing and impedance sensing capabilities. A sensor switch is provided to advantageously switch between heart rate monitoring and minute volume monitoring in a way that provides sensitive apnea detection with efficient use of battery energy. In yet another embodiment, conversion from heart rate monitoring to a method based on QT-interval variation is performed when a patient's intrinsic heart rate is not available due to bradycardia pacing. In lieu of the foregoing at least two sensors may be used alone or in combination. That is, each respective output may be compared to confirm another sensor output signal.

Cyclical variations of the chosen monitored parameter may be determined based on a method of threshold crossing detections or based on the detection of intervals of a progressively changing signal. A preliminary cycle detection is subjected to a set of criteria or rules required to be met before verifying the cycle as evidence of apnea. In a preferred embodiment, a cycle duration length is determined and compared to a predetermined apnea-hyperpnea cycle duration range in order to verify a detected cycle as a valid apnea-hyperpnea cycle. A predetermined minimum number of consecutive cycles may also be required before verifying the detected cycles as a disordered breathing episode. Alternatively or additionally, a minimum difference between the maximum and minimum values of the cyclically varying parameter signal may be required to validate a detected cycle as an apnea-hyperpnea cycle.

A number of disordered breathing metrics may be determined based on detected cycles of the monitored parameter during a given monitoring period including, for example, any of the total number of cycles, total cycle length, mean cycle duration, minimum and maximum parameter values, an apnea-hypopnea index, and an apnea cycle index defined as the ratio of apnea-hyperpnea cycles to non-apnea cycles of the monitored parameter. Long-term and short-term trended data may be calculated from these metrics of disordered breathing for use in patient screening, diagnosis, prognosis, and therapy evaluation.

The methods provided by the present invention may be implemented in a monitoring device or in a device that is additionally capable of delivering a therapy, such as a pacemaker capable of delivering overdrive pacing during detected apnea. The monitoring may be short- or long-term. In the event that an array of therapies is available, the device may select the therapy that provides, or is deemed to provide, the best therapeutic result for a given patient or disordered breathing episode. The methods for detecting an apnea episode may thus be used for monitoring and diagnosing a condition and/or for triggering the delivery of an apnea therapy. The present invention advantageously provides reliable monitoring and detection of disordered breathing patterns without requiring special sensors or high computational burden.

DETAILED DESCRIPTION OF THE INVENTION

The present invention is primarily directed at providing a method for detecting disordered breathing patterns, which is readily implemented in an implantable device. The methods included allow monitoring of cyclical changes that occur in certain physiological signals during sleep disordered breathing, or other disordered breathing patterns such as Cheyne-Stokes breathing, for the purposes of screening, diagnosing, or monitoring these types of conditions. An implantable device in which these methods are implemented may be a monitoring device which detects disordered breathing episodes and stores the occurrence of detected episodes and/or any of a number of disordered breathing metrics allowing a physician to review the incidence of disordered breathing and track the patient's condition over time. For example, methods included in the present invention may be implemented in a minimally invasive ECG monitoring device, such as the minimally invasive implantable device for monitoring physiologic events generally disclosed in U.S. Pat. No. 5,987,352 issued to Klein et al., incorporated herein by reference in its entirety, by adding microprocessing capabilities for carrying out functions to be described herein. Alternatively, methods included in the present invention may be implemented in an implantable device that is additionally capable of delivering a therapy to alleviate a disordered breathing condition once it is detected. Such devices may include cardiac pacemakers or ICDs which deliver overdrive pacing to the heart in response to sleep apnea, diaphragm pacing devices, or other neuromuscular stimulators for stimulating the hypoglossal nerve, the central nervous system, skeletal muscles along the upper airway tract, or other neuromuscular tissue, or other devices intended to deliver a therapy for terminating or preventing an apnea episode. An implantable monitoring device could further be used in conjunction with external therapy devices, such as positive airway pressure devices, through telemetric communication. While implementation in an implantable device is preferred, methods included in the present invention may also be readily implemented in an external monitoring device or external monitoring plus therapy device.

Figure 1:
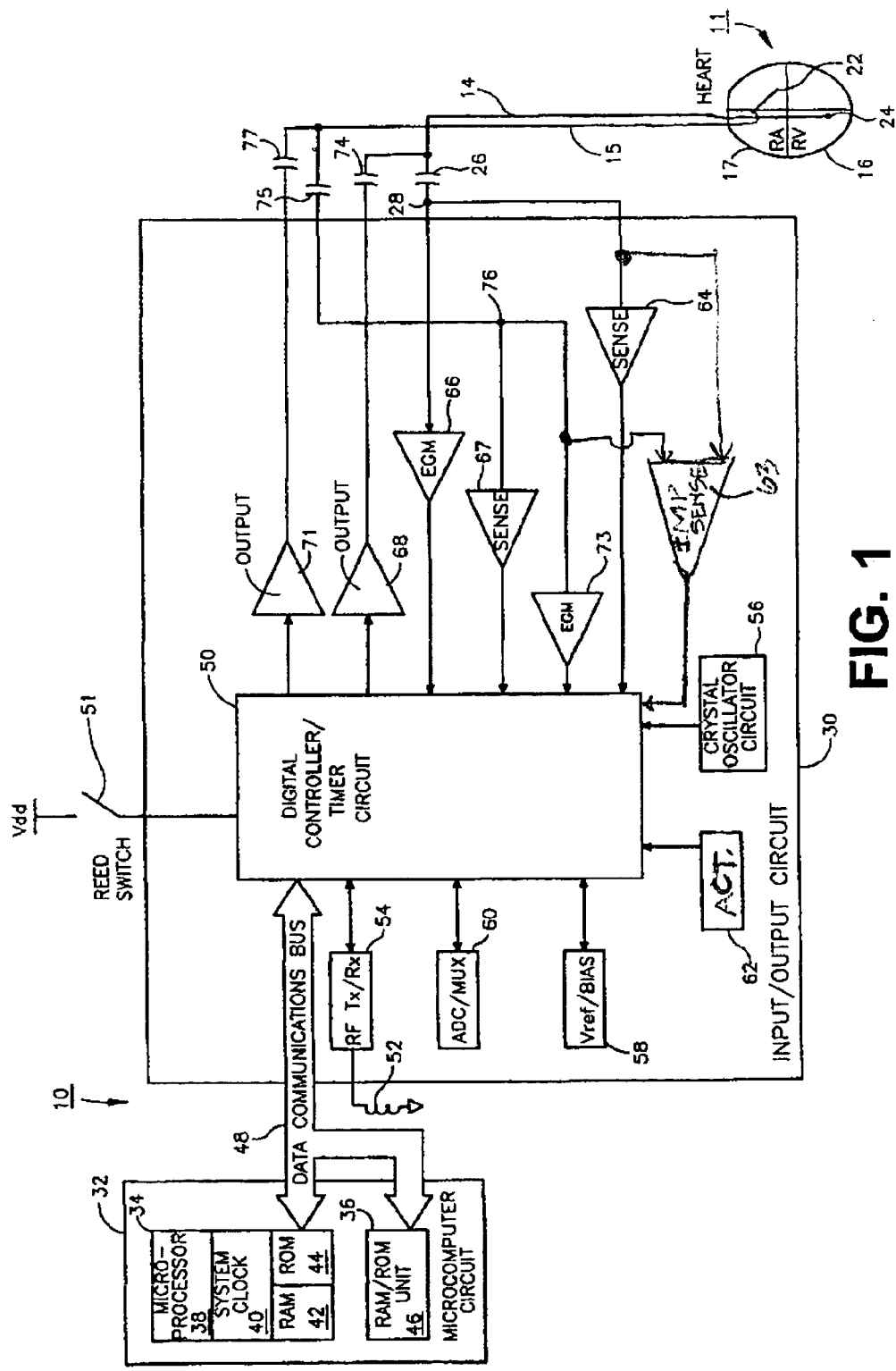
FIG. 1 is a functional block diagram of an exemplary implantable device in which the methods included in the present invention for monitoring disordered breathing may be implemented.

FIG. 1 is a functional block diagram of an exemplary implantable device in which the methods included in the present invention for monitoring disordered breathing may be implemented. Device 10 includes cardiac pacing capabilities and is coupled to the heart 11 by way of at least one cardiac lead for sensing an EGM signal and delivering cardiac pacing as needed. Lead 14 includes an endocardial electrode 24 located near its distal end and positioned within the right ventricle 16. Electrode 24 is electrically coupled by a conductor insulated within lead 14 to device 10 through an input capacitor 26 to a terminal 28. A second lead 15 includes a distally located endocardial electrode 22 positioned within the right atrium 17. Electrode 22 is electrically coupled by a conductor insulated within lead 15 to device 10 through an input capacitor 75 to a terminal 76. It is recognized that alternative lead and electrode systems may be used. For example, for the purposes of the present invention, dual chamber sensing is not required, and detection of a heart rate may be performed from sensing EGM signals in only one heart chamber. However, in the event that a patient has AV block the one chamber should most preferably not comprise a ventricular chamber and the sensed chamber should be one that senses "intrinsic heart rate." In addition, left ventricular sensing may be preferred for patients who have intact intrinsic conduction. That is, having a sense electrode disposed proximate the left ventricle or oriented to sense left ventricular depolarization events, as is known in the art.

Input/output circuit 30 contains the operating input and output analog circuits for digital controlling and timing circuits needed for the detection of P-waves and R-waves, and for the application of pacing pulses to the heart to control its rate under the control of software-implemented algorithms in a microcontroller 32. Cardiac signals sensed by the atrial electrode 22 are available as input to atrial sense amplifier 67 for the detection of atrial depolarizations, known as "P-waves". Cardiac signals sensed by the ventricular electrode 24 are available as input to ventricular sense amplifier 64 for the detection of ventricular depolarizations, known as "R-waves." Atrial sense amplifier 67 and ventricular sense amplifier 64 are preferably automatic gain controlled amplifiers with adjustable sensing thresholds. The general operation of the sense amplifiers 64 and 67 may correspond to that disclosed in U.S. Pat. No. 5,117,824, by Keimel, et al., incorporated herein by reference in its entirety. Whenever a signal received by the ventricular sense amplifier 64 exceeds a ventricular sensing threshold, an R-out signal is generated as output from sense amplifier 64 and received as input to digital controller and timer circuit 50. Likewise, whenever a signal received by atrial sense amplifier 67 exceeds an atrial sensing threshold, a P-out signal is generated as output from sense amplifier 67 and received as input to digital controller and timer circuit 50. P-out and R-out signals cause escape intervals, which are used to control the timing of pacing pulse delivery and are set by digital controller and timer circuit 50, to be reset. In accordance with one embodiment of the present invention, sensed P-P intervals or sensed R-R intervals, or the associated heart rate determined from these sensed intervals, are monitored for the detection of apnea.

Microcontroller 32 includes an on-board circuit 34 and an off-board circuit 36. On-board circuit 34 includes a microprocessor 38, a system clock 40, and onboard RAM 42 and ROM 44. Off-board circuit 36 includes a RAM/ROM unit 46. Microcontroller 32 is coupled to digital controller and time circuit 50 via a data communications bus 48. Microcontroller 32 may be fabricated from custom IC devices augmented by standard RAM/ROM components.

An antenna 52 is connected to input/output circuit 30 for purposes of uplink/downlink telemetery through a radio frequency (RF) transmitter/receiver 54. Telemetering both analog and digital data between antenna 52 and an external device, such as an external programmer (not shown), may be accomplished using numerous types of telemetry systems known in the art for use in implantable devices. Antenna 52 may also be used to receive telemetered signals from a patient activator that allows the patient to trigger certain device functions. In one embodiment of the present invention, disordered breathing monitoring may be triggered by the patient using a patient activator when he/she desires monitoring to commence, such as when going to bed at night. Patient activation devices are known in the art of cardiac rhythm management. Various mechanisms for patient-triggering of an implantable device function are generally described in the above-cited U.S. Pat. No. 5,987,352, issued to Klein et al.

A crystal oscillator circuit 56, typically a 32,768 Hz crystal-controlled oscillator, provides main timing clock signals to digital controller and timer circuit 50. A Vref/Bias circuit 58 generates a stable voltage reference and bias currents for the analog circuits of input/output circuit 30. An A/D converter and multiplexer circuit (ADC/MUX) 60 digitizes analog signals and voltages for uplinking and downlinking by telemetry, and for use by digital controller and timer circuit 50 and algorithms executed by microcontroller 32 during various device functions.

Operating commands for controlling the timing of the pacemaker are coupled by bus 48 to digital controller and timer circuit 50 wherein digital timers set escape intervals used for controlling the timing of pacing pulse delivery, as well as various refractory, blanking, and other timing windows for controlling the operation of the peripheral components within input/output circuit 30.

Digital controller and timer circuit 50 is further coupled to electrogram (EGM) amplifiers 66 and 73 for receiving electrogram signals, which may be transmitted by uplink telemetry to an external device. Electrogram signals are also available for further waveform processing by microcontroller 32. In accordance with one embodiment of the present invention, EGM signals may be analyzed for Q-T interval length such that monitoring of Q-T interval changes may be performed for detecting apnea.

Output pulse generators 68 and 71 provide pacing stimuli to the patient's heart 11 through output capacitors 74 and 77 and leads 14 and 15 in response to pace trigger signals received from digital controller and timer circuit 50 each time an escape interval times out or in response to other stored commands. Device 10 may be capable of various operating modes known in the art such as DDD, DDI, VVI, VOO, AOO, VDD, DVI, AAI, ADI, AAT and VVT and the like. Device 10 may further be capable of delivering pacing pulses in a rate-responsive mode such as DDDR, DDIR, AAIR, ADIR, VVIR, VOOR and VVTR and the like.

In response to the detection of a disordered breathing pattern, pacing pulses may be applied to the heart at a higher than normal rate, e.g. 90 bpm. A device for treating sleep apnea by stimulating the heart at a higher rate than the heart's natural rate is generally disclosed in the above-cited U.S. Pat. No. 6,126,611 issued to Bourgeois et al.

In some embodiments of the present invention, device 10 preferably includes an impedance sensing circuit 63. Impedance sensing circuit 63 may be used for measuring thoracic impedance for the purposes of deriving a minute volume. For the purposes of the present invention, any method known in the art for measuring an impedance and deriving minute volume may be used. In a preferred embodiment, minute volume measurement is performed according to the methods employed by the commercially available Medtronic Kappa® 400 Pacing System. The entire minute volume determination methodology of the Kappa 400 Pacing System is retained in the disclosed embodiment of the present invention. Various alternative methods and apparatus for measuring a patient's minute volume in rate-responsive pacemakers are generally disclosed in U.S. Pat. No. 6,334,071 issued to Lu, U.S. Pat. No. 5,562,712 issued to Steinhaus et al., U.S. Pat. No. 5,507,785 issued to Deno, and U.S. Pat. No. 4,901,725 issued to Nappholz et al., all of which patents are hereby incorporated herein by reference in their entirety. As will be described below, minute volume monitoring is performed in some of the embodiments of the present invention for detecting disordered breathing.

Device 10 may further include an activity sensor 62. An activity sensor may be incorporated as a piezoelectric element sensitive to body movements such that a signal from the activity sensor is correlated to the level of a patient's activity. The use of activity sensors is known in the art of rate-responsive pacemakers. An activity sensor may be implemented as generally disclosed in commonly assigned U.S. Pat. No. 5,052,388, issued to Sivula et al., incorporated herein by reference in its entirety.

Alternative implementations of activity sensors for use in rate-responsive pacemakers are generally disclosed in U.S. Pat. No. 4,428,378 to Anderson; U.S. Pat. No. 4,896,068 to Nilsson; U.S. Pat. No. 4,869,251 and to Lekholm et al., all of which patents are incorporated herein by reference in their entirety. The activity sensor 62 may be used in the determination of a sensor-indicated base pacing rate. Activity sensor 62 may be used as a sensor cross-check to verify that a provisionally detected sleep apnea episode is occurring when the patient is at a resting level of activity.

In accordance with one embodiment of the present invention, the activity sensor 62 may be used in detecting a sleep state. Methods for detecting when a patient is likely to be asleep are known for use in cardiac rhythm management devices. Such methods may be based on one or more sensor inputs in conjunction with a real-time clock. Sensor signals that may be used for detecting a sleeping state may include an activity sensor, a respiration sensor, a posture sensor, a blood temperature sensor, etc. An implantable multi-axis position and activity sensor is disclosed in U.S. Pat. No. 5,233,984, issued to Thompson, incorporated herein by reference in its entirety. A device capable of determining when a patient is likely to be asleep is disclosed in U.S. Pat. No. 5,630,834, issued to Bardy and U.S. Pat. No. 5,814,087 issued to Renirie, both incorporated herein by reference in its entirety.

Detection of arousal from sleep may be based on time of day or determined based on a reversal of other signals used to detect sleep. A method for detecting awakening by monitoring changes in QT interval is generally disclosed in U.S. Pat. No. 6,161,041 issued to Stoop et al., incorporated herein by reference in its entirety. A method for detecting arousal by monitoring respiratory effort is disclosed in U.S. Pat. No. 5,485,851 issued to Erickson, incorporated herein by reference in its entirety. The reader should note that "arousal" monitoring and "state-of-wakefulness" are different concepts since arousal could be just autonomic arousal and may not involve "consciousness" detection. Here, arousals due to apnea usually last for a short period and immediately followed by another apnea/hypopnea event, but "awake state" is preferably confirmed by "5-30 minute" sensor information sets that consistently indicate the state (e.g. high variability in MV, act counts as well as continuous presence of activity counts). In case of posture sensor, upright posture in corroboration with other sensors usually means the state of awake.

Figure 2:
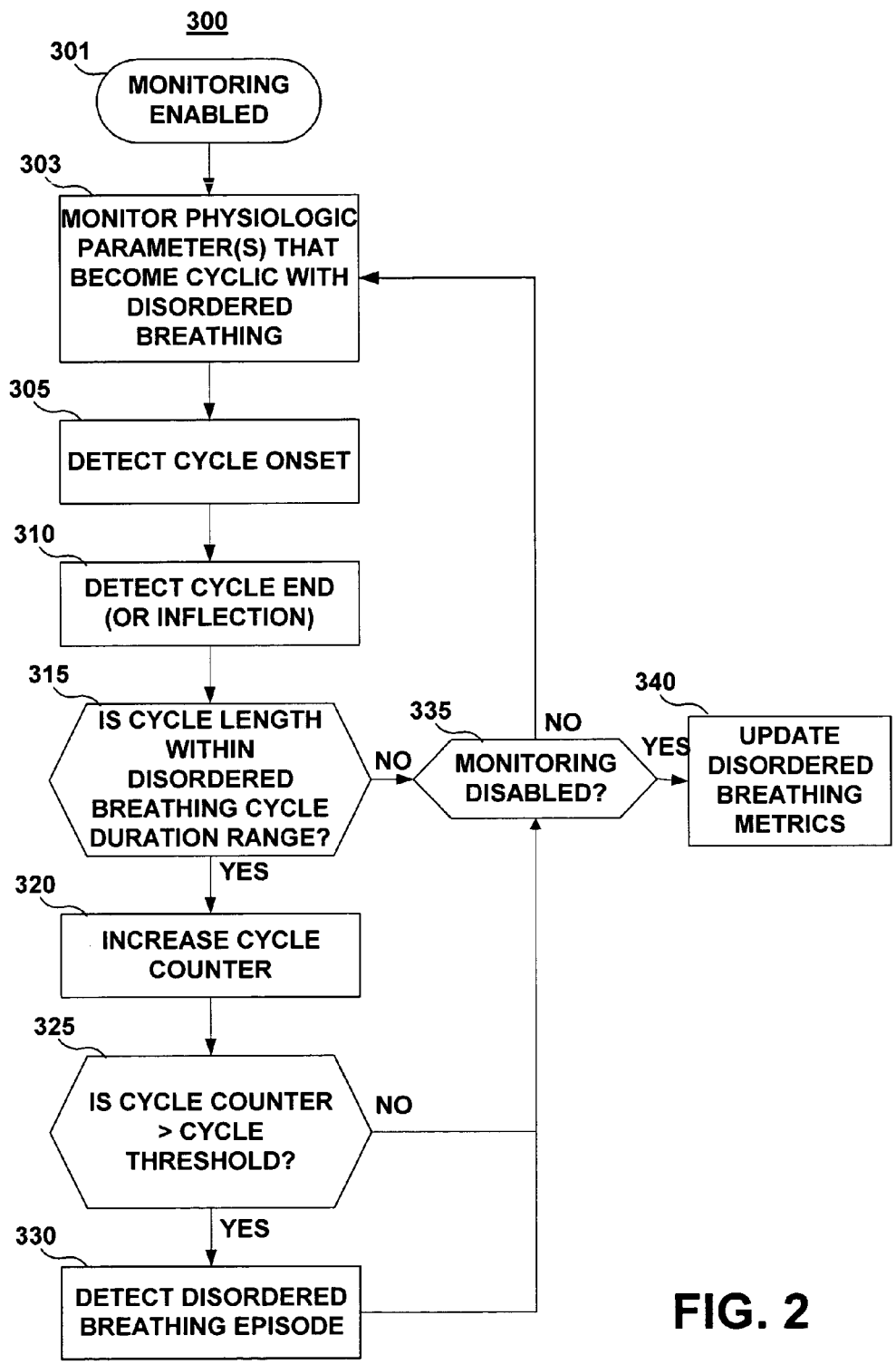
FIG. 2 is a flow chart providing an overview of a method for monitoring for sleep apnea, Cheyne-Stokes breathing, or other types of respiration rate abnormalities in accordance with the present invention, referred to herein inclusively as "disordered breathing".

FIG. 2 is a flow chart providing an overview of a method for monitoring for sleep apnea, Cheyne-Stokes breathing, or other types of respiration rate abnormalities in accordance with the present invention, referred to herein inclusively as "disordered breathing". Method 300 is initiated at step 301 when disordered breathing monitoring is enabled. Monitoring may be enabled to operate continuously such that detection of disordered breathing may be made day or night, for example for monitoring for Cheyne-Stokes breathing. Monitoring may alternatively be enabled during prescribed periods of day based on a real-time clock or timer function, for example at night when the patient is expected to be asleep to monitor for sleep apnea. Monitoring may alternatively be enabled by an automatic triggering event. For example, monitoring for sleep apnea may be automatically enabled when a patient is detected to be at rest or asleep according to sleep detection methods as described above. Monitoring may be disabled by a real-time clock or timer function according to a programmable monitoring period or disabled by an automatic triggering event, such as detection of arousal as described above. Monitoring may additionally or alternatively be enabled and/or disabled by a manual trigger delivered by the patient, for example when he/she is going to sleep using a means of telemetric activator. Such manual triggering to enable monitoring may be followed by a monitoring delay in order to allow the patient time to fall asleep before monitoring commences. However, to avoid problems associated with patient non-compliance, automatic monitoring is generally preferred over manually-triggered monitoring.

At step 303, a physiological parameter is monitored, which is known to undergo cyclic oscillations corresponding to cyclic disordered breathing patterns, such as successive apnea or hypopnea (or apnea-arousal) episodes that occur during sleep apnea or Cheyne-Stokes breathing. In one embodiment, heart rate is monitored at step 303 as will be described in greater detail in conjunction with FIG. 4. Alternating periods of bradycardia and tachycardia are observed to occur concurrently with apnea and hyperpnea periods, respectively, associated with sleep apnea. Detection of this cyclic variation in heart rate may advantageously be used for detecting an episode of sleep apnea.

In an alternative embodiment, minute volume is monitored at step 303 as will be described in greater detail in conjunction with FIG. 8. Minute volume is a direct measurement of the decreased respiratory function during apnea and the increased respiratory function during hyperpnea (or arousal).

In yet another embodiment, as will be described in conjunction with FIG. 11, a combination of heart rate and minute volume monitoring may be performed for monitoring disordered breathing. Alternative embodiments may involve monitoring of other physiological parameters that become cyclic during disordered breathing characterized by alternating periods of apnea and hyperpnea. Such parameters may include Q-T interval, Stim-T interval, oxygen saturation, other possibilities include sensing blood pressure, PCO2, SaO2, or ePAD, and the like. In one embodiment, two or more physiological parameters may be monitored concurrently in order to detect cyclic patterns indicative of disordered breathing to avoid false positive or false negative detections of disordered breathing that might occur based on monitoring a single parameter.

At step 305, a change in the monitored physiological parameter indicating the onset of a cyclic change that may be associated with disordered breathing is detected. At step 310, the end point, or alternatively an inflection point, of the cyclic change is detected. Methods used for detecting a cyclic change in a monitored parameter may vary depending on the parameter used. Methods for detecting cyclic changes in heart rate associated with cyclic disordered breathing patterns will be described in conjunction with FIG. 4 below. Methods for detecting cyclic changes in minute volume will be described in conjunction with FIG. 8 below.

After provisionally detecting a disordered breathing cycle, one or more criteria or rules are applied to verify that the detected cycle is a valid apnea cycle. Such rules may relate to, but are not limited to, the cycle period (also termed "cycle length"), maximum and minimum amplitudes, and number of consecutive cycles detected. In a preferred embodiment, at least a criterion related to the cycle period is applied. At decision step 315, the detected cycle length is compared to a cycle duration range associated with the disordered breathing pattern of interest. For example, one apnea-hyperpnea cycle occurring during sleep apnea may have a typical duration of a minimum of about 25 to a maximum of about 120 seconds. If the detected cycle length of the monitored parameter is greater than the minimum duration and less than the maximum duration considered indicative of a disordered breathing pattern, the provisionally detected apnea-hyperpnea cycle is validated, and a cycle counter is increased at step 320. If the decision at step 315 is negative, monitoring of the physiological parameter(s) continues at step 303 as long as monitoring is enabled, as determined at decision step 335.

The cycle counter is compared to a minimum number of consecutive cycles required for detecting the disordered breathing pattern of interest at step 325. For example, at least two validated apnea-hyperpnea cycles occurring consecutively may be required for detecting sleep apnea. A cycle threshold criteria is preferably programmable and may have a value of one or more. If the cycle threshold criteria is met at decision step 325, the disordered breathing pattern of interest is detected at step 330. If the decision at step 325 is negative, monitoring of the physiological parameter continues at step 303 as long as monitoring is enabled, as determined at decision step 335.

Figure 3:
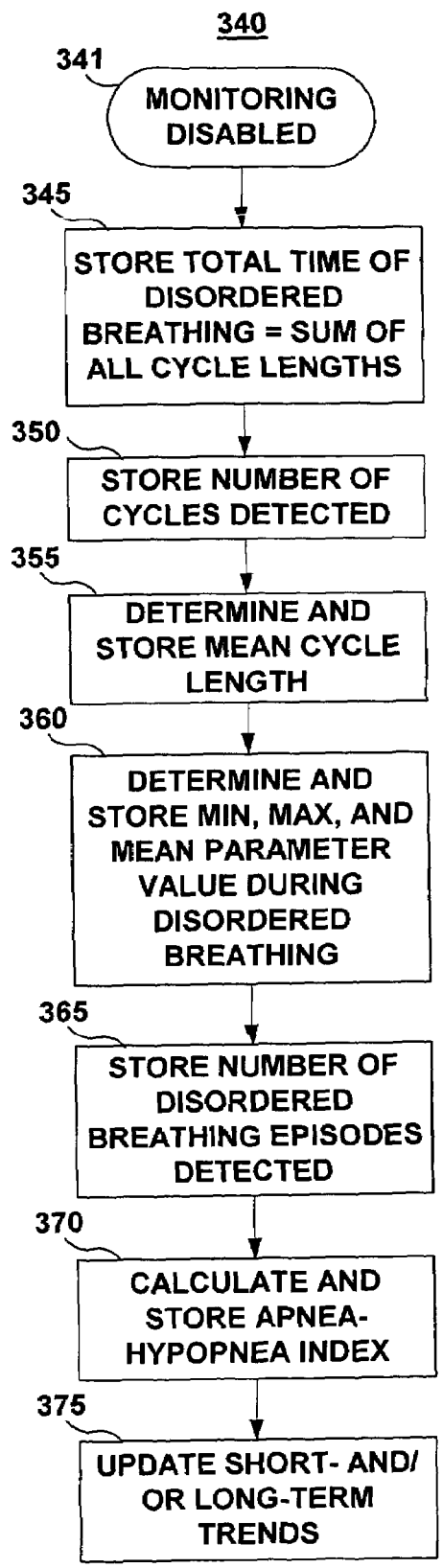
FIG. 3 is a flow chart providing an overview of disordered breathing metrics that may be updated following a monitoring period.

Once a monitoring period is expired or automatically or manually disabled, monitored disordered breathing metrics may be updated and stored in device memory. FIG. 3 is a flow chart providing an overview of disordered breathing metrics that may be updated following a monitoring period. At step 341, a monitoring period is disabled triggering the updating of stored disordered breathing metrics. At step 345, the total time of disordered breathing detected during the monitoring period is calculated as the summation of all detected and validated cycle lengths during the monitoring episode.

At step 350, the total number of valid cycles detected during the monitoring period may be stored, and at step 355 the mean cycle length may be determined and stored. At step 360, the overall minimum, maximum, and mean value of the monitored parameter during detected disordered breathing episodes may be stored with the total number of detected disordered breathing episodes being stored at step 365.

Any or all of these breathing disorder metrics may be stored after a monitoring period is terminated, as indicated in FIG. 3. Alternatively, any of these metrics may be updated following each detection of a disordered breathing episode rather than at the conclusion of a monitoring period.

If the total monitoring time is available, an apnea-hypopnea index (AHI) may be calculated at step 370 from the number of valid cycles detected divided by the monitoring time. At step 375, a short-term, for example weekly, and or a long-term, for example monthly, average of any of the monitoring metrics determined and stored for the current monitoring period may be updated. Such trended data provides a physician with changes in the patient condition due to a worsening disease state or a therapy response. It is recognized that metrics of disordered breathing other than those indicated in FIG. 3 may be defined based on the monitored physiological parameter(s). Stored breathing disorder metrics may be uplinked to an external device upon interrogation by a user, providing useful information to a physician in diagnosing or screening for sleep apnea, Cheyne-Stokes breathing or other breathing abnormalities; in prescribing or evaluating a therapy; or for use as a prognostic indicator of a patient condition.

Trends in stored breathing disorder metrics over relatively short-term or long-term periods may also be determined, stored, and made available to a physician for evaluating changes in a patient's condition over time, for example in response to a therapy. At step 375, short-term and long-term trended data is updated. Such trended data may include, for example, weekly or monthly mean AHI, mean cycle length, mean number of disordered breathing episodes or mean total disordered breathing time.

Figure 4:
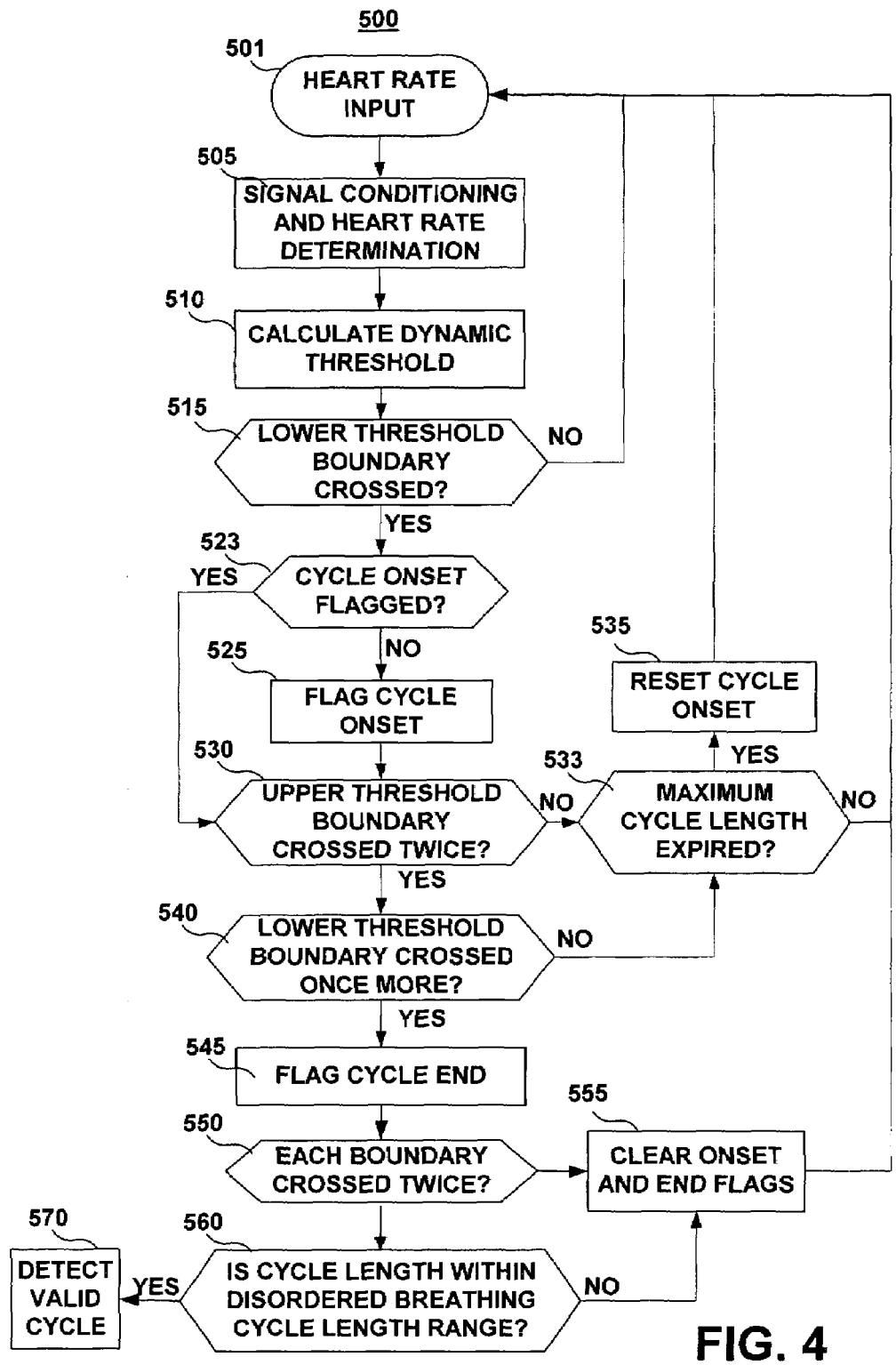
FIG. 4 is a flow chart summarizing the steps included in a method for monitoring changes in heart rate as an indicator of disordered breathing.

FIG. 4 is a flow chart summarizing the steps included in a method for monitoring changes in heart rate as an indicator of disordered breathing. At step 501, a heart rate signal is received. A heart rate signal could be a sensed ECG or EGM signal from which atrial P-P intervals or ventricular R-R intervals may be derived from sensed P-waves or R-waves, respectively. A heart rate signal could alternatively be a pulse pressure signal, heart wall motion signal, or any other signal from which the heart rate may be derived. In a preferred embodiment, the heart rate signal input is provided as sensed R-R or P-P intervals.

At step 505, the heart rate signal input undergoes signal conditioning to reduce the effect of noise and eliminate and outlying data points. Signal conditioning may employ a median filter which determines the median value of a given number, for example 3 to 5, of the most recent input values, such as P-P or R-R intervals. The median input value may then be used to determine a current heart rate such that oscillations in heart rate that may correspond to disordered breathing may be detected. Conversion of the heart rate input to an actual heart rate is optional. Intervals associated with sensed P-waves, R-waves, pulse pressure, heart wall motion, etc., may be used directly without a converting to a heart rate. In such embodiments, cyclic oscillations between longer intervals (slow heart rate) and shorter intervals (faster heart rate) may be detected as an indication of sleep disordered breathing. For the sake of simplifying the description provided herein, the method of FIG. 4 will be described in terms of a heart rate.

At step 510 a dynamic threshold is calculated based on the sensed heart rate. In one embodiment, the dynamic threshold may be a range defined by upper and lower threshold boundaries that, when crossed, indicates a change in heart rate that may be associated with a disordered breathing cycle. In a preferred embodiment, a dynamic threshold may be calculated based on a function of the rolling mean of the sensed heart rate. A rolling mean heart rate may calculated from a given number of heart rate data points according to the following formula:

$$HR_{mean}(n) = HR_{mean}(n-1) + \frac{x(n) - HR_{mean}(n-1)}{N}$$

wherein $HR_{mean}(n-1)$ is the rolling heart rate calculated on the previous heart rate data point; $x(n)$ is the current heart rate data point; and N is the number of data points included in the rolling average. The upper and lower boundaries of the dynamic threshold range (DTR) may then be calculated according to equation (2):

$$DTR(n) = HR_{mean}(n) \pm K(n)$$

wherein $K(n)$ may be a fixed value including 0, a fraction of the mean heart rate from equation (1), proportional to the standard deviation of the mean heart rate, or other predefined value. When $K(n)$ is 0, the dynamic threshold is a single curve rather than a range defined by an upper boundary curve and a lower boundary curve. In alternative embodiments, a threshold value or threshold range may be fixed value(s) that are programmable, rather than dynamically calculated values.

At decision step 515 of FIG. 4, the heart rate is monitored until it crosses a lower dynamic threshold boundary. When the lower threshold boundary is crossed, and if a cycle onset flag is not already set as determined at decision step 523, a cycle onset time is flagged at step 525. The heart rate is then monitored at step 530 to determine if the heart rate increases again and crosses the upper threshold in an upper direction and again decreases to cross the upper threshold in a downward direction. If no crossing of the upper dynamic threshold boundary, or only one upward crossing but no downward crossing, is detected, the time expired since the cycle onset flag is compared to a maximum cycle length at decision step 533. If the maximum cycle length has expired, the cycle onset flag is cleared at step 535, and the method 500 returns to step 501 to continue monitoring the heart rate signal input as long as monitoring is enabled.

If the maximum cycle length has not yet expired at decision step 533; the method 500 continues to monitor the heart rate until an upward crossing followed by a downward crossing of the upper dynamic threshold boundary is detected at step 530. At step 540, the method 500 determines if heart rate again crosses the lower threshold boundary. If the heart rate does not cross the lower threshold boundary prior to the maximum cycle length expiring at step 533, the cycle onset flag is cleared at step 535, and the method 500 returns to step 501 to continue monitoring heart rate.

If the heart rate crosses the lower threshold boundary again (step 540) after crossing the upper threshold boundary twice (step 530), the time of the lower threshold crossing is flagged as the cycle end at step 545. At step 550, the method 500 verifies that neither threshold boundary was crossed more than twice in a row. If the heart rate crosses a threshold boundary three or more times before crossing the other threshold boundary, the detected oscillations in heart rate are not considered a valid cycle for the detection of disordered breathing. If the same threshold was crossed more than twice in a row, as determined at step 550, the cycle is rejected and the cycle onset and end flags are cleared at step 555. The method 500 returns to step 501 to monitor the heart rate.

At step 560, the cycle length, determined as the difference between the flagged onset time and end time, is compared to a predefined cycle length range associated with the disordered breathing pattern of interest. If the heart rate has crossed the upper and lower threshold boundaries each twice, without crossing either boundary more than twice before crossing the other threshold boundary, within the predefined cycle time range, the detected cycle is classified as a valid disordered breathing cycle at step 570.

In other embodiments, alternative or additional criteria may be defined, which must be met in order to detect a valid cycle. Such alternative criteria may include the number of inflections within or outside of the threshold range, the maximum or minimum heart rates, or other criteria. Once a valid cycle is detected, the cycle counter may be increased at step 320 of FIG. 2, and the method 300 may proceed with determining if a required number of cycles have been detected to verify detection of a disordered breathing episode. Thus, a disordered breathing cycle may be identified based on the periodicity, amplitude change, and morphology of heart rate oscillations. Because special patient conditions may exist which affect these features of heart rate changes during a disordered breathing episode, such as prescribed drugs the patient may be taking or other pathological conditions, criteria for validating a detected cycle are preferably programmable such that they may be tailored to an individual patient.

Figure 5A:
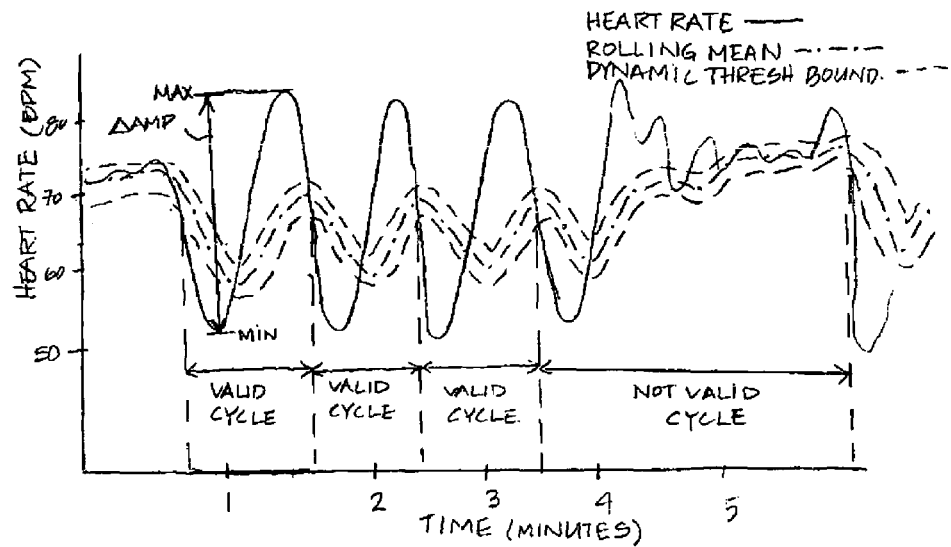
FIG. 5A is a graph depicting heart rate oscillations that can occur during sleep apnea.

FIG. 5A is a graph depicting heart rate oscillations that can occur during sleep apnea. Time is plotted on the horizontal axis in minutes and heart rate is plotted on the vertical axis in beats per minute (BPM). The rolling mean heart rate, as determined at signal conditioning step 505 in FIG. 4 is shown by dashed-dotted line. Upper and lower dynamic threshold boundaries, calculated based on the rolling mean at step 510 in FIG. 4, are indicated by dashed line. The onset of a heart rate cycle is marked by a (downward) crossing of the lower dynamic boundary. The heart rate then crosses the upper dynamic boundary as it increases before decreasing. The next downward crossing of the lower dynamic boundary marks the end of the cycle and the start of a subsequent cycle. Valid cycles are indicated as cycles meeting detection criteria which may include cycle duration criteria and cycle amplitude criteria. The cycle duration preferably is required to fall within a predetermined disordered breathing cycle range as described above. Another criteria may require a minimum difference between the maximum heart rate and minimum heart rate, shown as ΔAMP in FIG. 5A, occurring during a provisionally detected cycle. In FIG. 5A, three valid cycles are detected followed by a provisionally detected cycle onset determined to be invalid due to more than two crossings of the upper threshold boundary before a second downward crossing of the lower boundary.

Figure 5B:
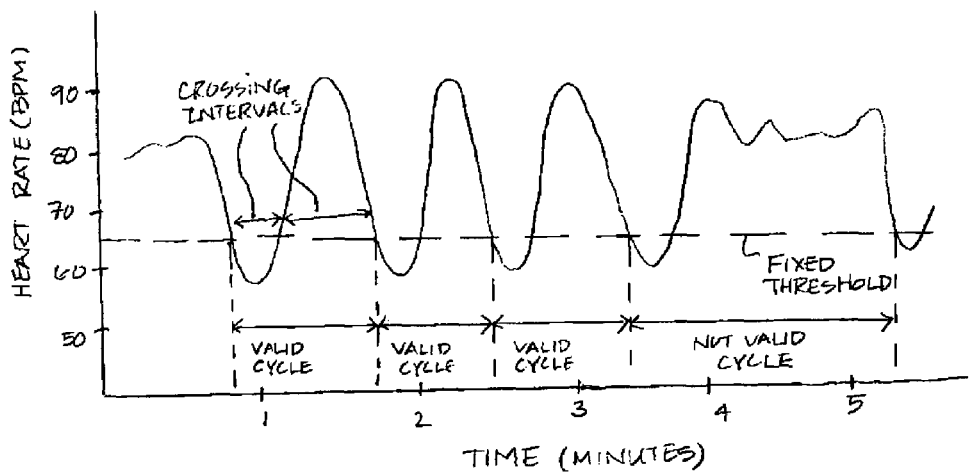
FIG. 5B is a graph depicting cycle detection based on crossings of a single threshold.

FIG. 5B is a graph depicting cycle detection based on crossings of a single threshold. A single threshold may be a rolling mean, as illustrated in FIG. 5A, or a fixed value as illustrated by dashed line in FIG. 5B. The fixed threshold may be programmed by a clinician. A downward threshold crossing can be designated as a cycle onset. A provisionally detected cycle can be indicated by a downward crossing followed by a single upward crossing and another downward crossing. The provisionally detected cycle can be validated according to cycle length and cycle amplitude criteria as described above. Alternative cycle validation criteria may be defined. For example, the intervals between threshold crossings (indicated in FIG. 5B as "crossing intervals") may be required to meet predetermined minimum and/or maximum time criteria. It is recognized that numerous variations of rules or criteria defining a valid cycle may be defined.

As noted above, an apnea-hypopnea index (AHI), measured as the number of apnea and hypopnea events per hour of sleep is commonly used to rate the severity of a sleep apnea condition. A reduction in AHI is used as a marker of improvement in the sleep apnea condition following a therapeutic intervention. In the present invention, AHI may be estimated by dividing the total number of detected cycles during a monitoring period divided by the monitoring period length. An alternative index, sometimes referred to herein as an "apnea cycle index," and other times referred to as sleep disordered breathing index (SDBI) or disordered breathing index (DBI)—consistent with the definition of breathing disorders provided herein—for determining the severity of a sleep apnea condition may be defined based on the ratio of apnea-hyperpnea cycles to normal breathing cycles during a monitoring period. The apnea cycle index (or SDBI/DBI) may be suitable for estimation of a patient's AHI by simply adding a total number of events and dividing it by number of hours monitored. However, for the ratio of Apnea-arousal cycles to normal breathing cycles, a different term should be used for clarity. The present invention provides a method for determining an apnea cycle index based on the detection of apnea-hyperpnea cycles based on heart rate monitoring. The time that the patient was actually asleep is not needed for determining the apnea cycle index.

Figure 6A:
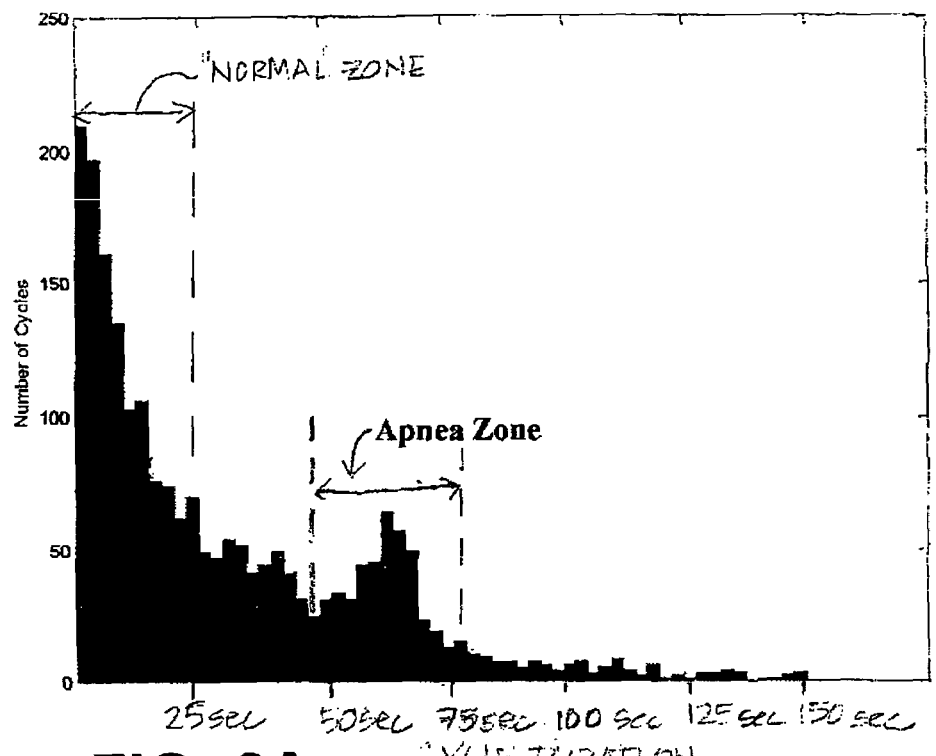
FIG. 6A is a sample histogram depicting the time duration of heart rate cycles in a patient suffering from severe sleep apnea.

FIG. 6A is a sample histogram depicting the time duration of heart rate cycles in a patient suffering from severe sleep apnea. Heart rate cycles less than approximately 25 seconds in duration are typical during normal breathing. The majority of heart rate cycles measured occur in this range, which may be defined as a "normal" zone of heart rate cycle durations. Heart rate cycles in the range of approximately 40 to 80 seconds are representative of apnea-hyperpnea cycles associated with sleep apnea. This range of heart rate cycle durations may be defined as an "apnea" zone. The apnea zone may vary between individuals.

Figure 6B:
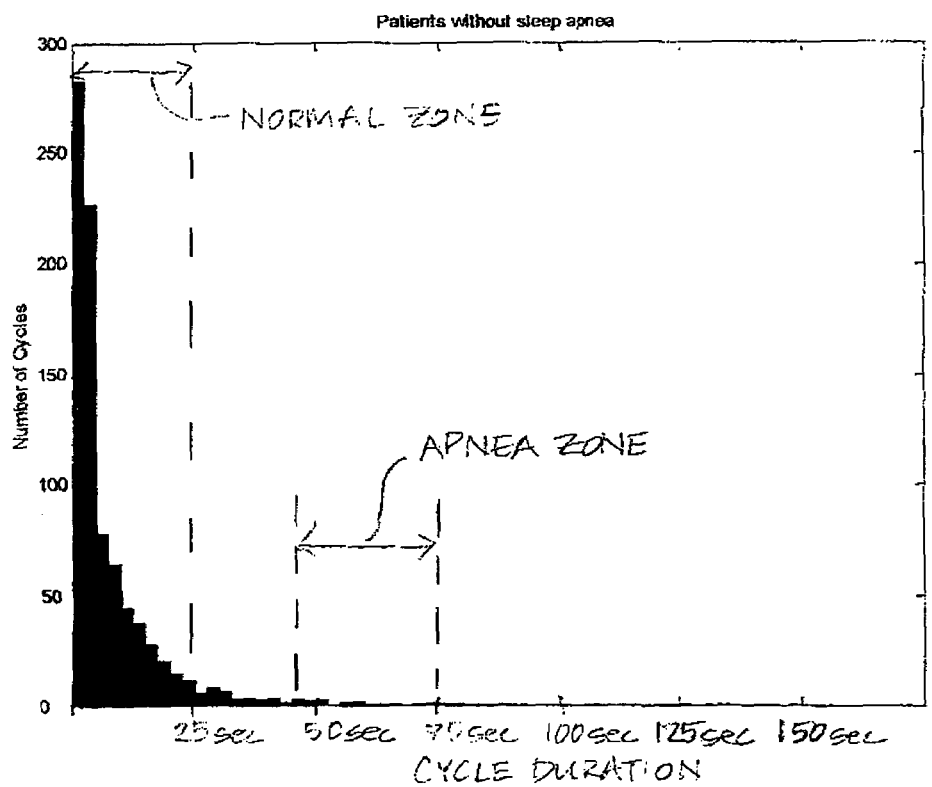
FIG. 6B is a sample histogram depicting the time duration of heart rate cycles in a patient without clinically significant sleep apnea.

In contrast, FIG. 6B is a sample histogram depicting the time duration of heart rate cycles in a patient without clinically significant sleep apnea. Very few heart rate cycles in the apnea zone are detected with nearly all heart rate cycles having a duration that may be associated with normal respiration.

Figure 7:
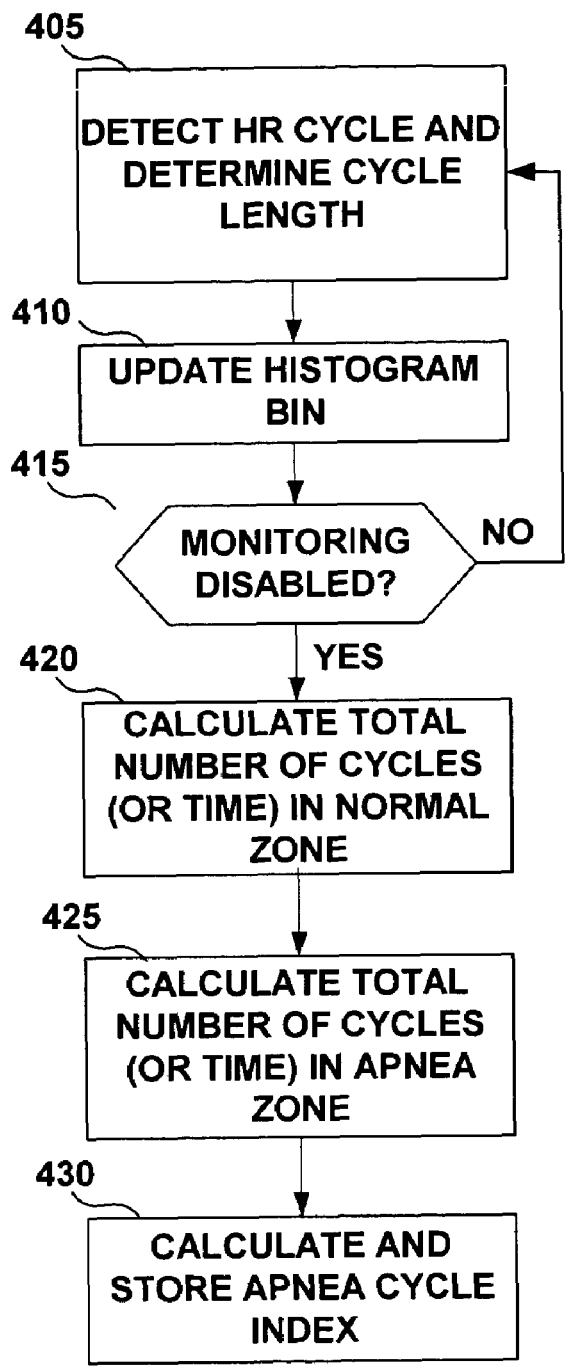
FIG. 7 is a flow chart summarizing the steps included in a method for determining an apnea cycle index that may be used for sleep apnea screening or diagnosis in accordance with the present invention.

FIG. 7 is a flow chart summarizing the steps included in a method for determining an apnea cycle index that may be used for sleep apnea screening or diagnosis in accordance with the present invention. At step 405, a heart rate (HR) cycle is detected and the length of the detected HR cycle is determined in accordance with the methods described above. A number of histogram bins are assigned a range of heart rate cycle durations. The histograms bins are used to count the number of heart rate cycles occurring in a given duration range. A histogram bin associated with the length of each heart rate cycle detected, whether it meets the apnea duration criteria or not, is increased by one at step 410. This process of detecting a heart rate cycle (step 405) and updating a histogram bin according to the HR cycle length (step 410) continues until monitoring is disabled at step 415.

After the monitoring period, the total number of HR cycles occurring in a predefined "normal" zone is determined at step 420 as the sum of all histogram bins falling within the normal zone. The normal zone may be defined as the range of HR cycle durations expected to occur during normal respiration, for example less than 25 seconds. At step 425, the total number of cycles occurring in a predefined "apnea" zone is determined as the sum of all histogram bins falling within the apnea zone. The apnea zone may be defined as the range of HR cycle durations expected to occur during apnea, for example in the range of 40 seconds to 80 seconds. Alternatively, the estimated total respiration time in the normal zone may be determined at step 420 by summing the products of each histogram bin value in the normal zone and the associated time duration as given by the following equation:

$$\text{Normal respiration time} = \sum_{i=Normal_{min}}^{i=Normal_{max}} H(i) \times duration_i$$

wherein $H(i)$ represents the value of the $i^{th}$ histogram bin; $duration_i$ represents the cycle duration associated with the $i^{th}$ histogram bin; and $normal_{min}$ and $normal_{max}$ represent the minimum and maximum HR cycle durations, respectively, defining the normal zone.

Likewise, at step 425, the estimated total respiration time in the apnea zone may be determined by summing the products of each histogram bin value in the apnea zone and the associated time duration as given by:

$$\text{Apnea respiration time} = \sum_{i=apnea_{min}}^{i=apnea_{max}} H(i) \times duration_i$$

wherein H(i) represents the value of the i$^{th}$ histogram bin; duration$_j$ represents the cycle duration associated with the i$^{th}$ histogram bin; and apnea$_{min}$ and apnea$_{max}$ represent the minimum and maximum HR cycle durations, respectively, defining the apnea zone.

The apnea cycle index may then be calculated at step 430 as the ratio of the total number of apnea cycles to the total number of normal cycles. Alternatively the apnea cycle index may be calculated as the ratio of the estimated apnea respiration time to the normal respiration time calculated according to equations 2 and 1, respectively.

The value of the apnea cycle index may be categorized according to relative severity with a high apnea cycle index indicating a more severe condition and relatively low apnea cycle index indicating a normal condition. Intermediate apnea cycle index ranges for mild and moderate conditions may be defined between the normal and severe condition ranges. The total time spent in apnea may similarly be categorized from normal to severe conditions. An exemplary categorization of apnea severity based on total apnea cycle time during an 8-hour night-time monitoring period is:

Normal: less than 30 minutes of apnea cycle time;

Mild: greater than 30 but less than 60 minutes of apnea cycle time;

Moderate: greater than 60 but less than 120 minutes of apnea cycle time;

Severe: more than 120 minutes of apnea cycle time.

While the method shown in FIG. 7 is based on determination of heart rate cycles, other physiological parameter cycles may be used for determining an apnea cycle index based on a ratio of apnea related cycles or time to normal related cycles or time.

Figure 8:
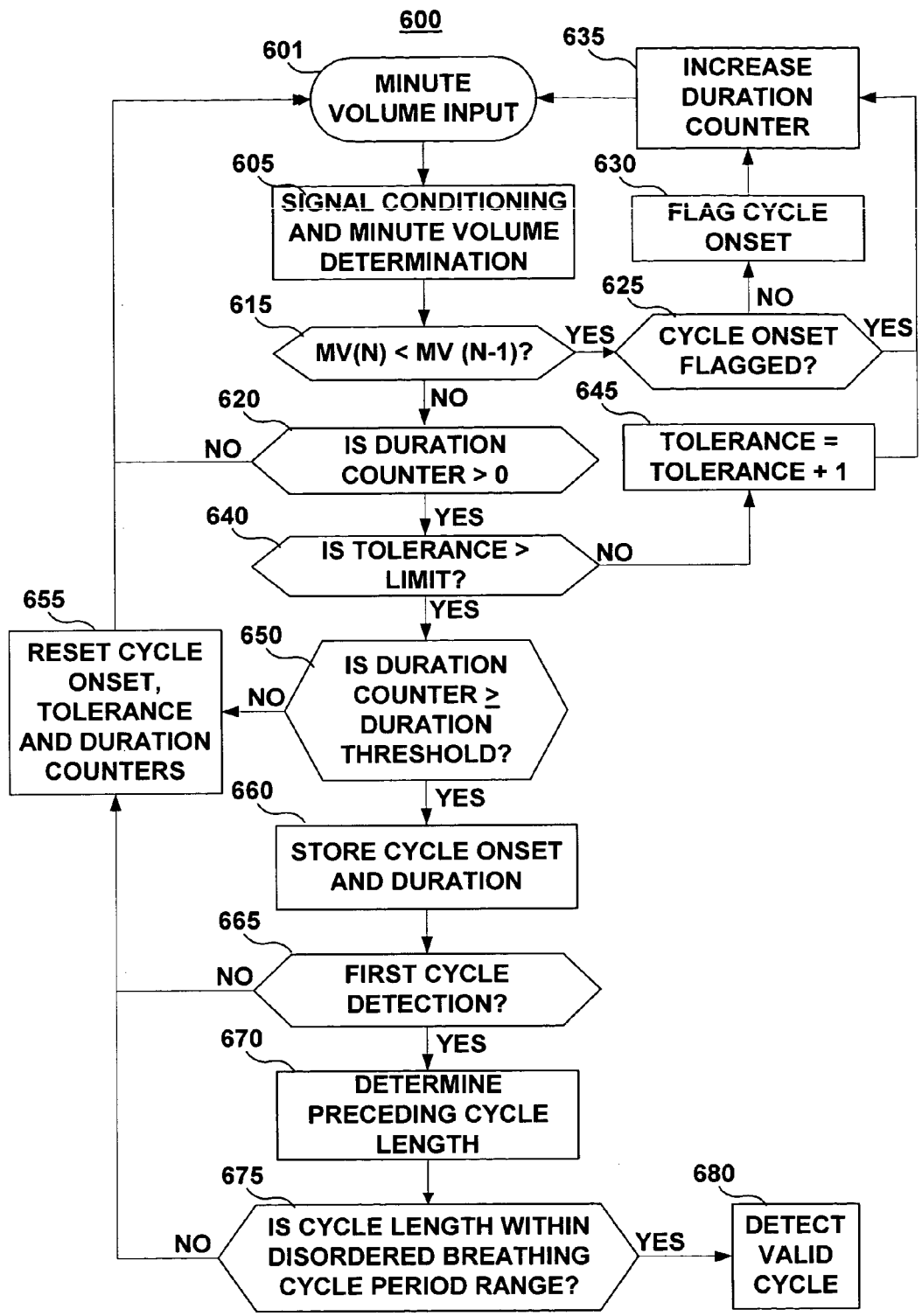
FIG. 8 is a flow chart summarizing the steps included in an alternative embodiment for monitoring oscillations of a physiological parameter due to disordered breathing.

FIG. 8 is a flow chart summarizing the steps included in an alternative embodiment for monitoring oscillations of a physiological parameter due to disordered breathing. In this embodiment, disordered breathing monitoring may be based on monitoring minute volume (MV), though other respiratory-related parameters or other physiological parameters that oscillate in concurrence with apnea-hypopnea cycles associated with disordered breathing could also be used.

At step 601, the monitored parameter input is received, which in this exemplary embodiment is minute volume (MV). Minute volume input may be determined from impedance measurements as described above. At step 605, the MV input undergoes signal conditioning to smooth the signal for eliminating noise. In a preferred embodiment, signal conditioning employs a three-point median filter. The sampling rate of an impedance signal used for determining minute volume is preferably on the order of 2 Hz. However, if implemented with an impedance sensing circuit (for respiration), then the sample rate should be preferably 4 Hz. In addition, the sampling rate may be increased (to about 16 Hz), but for input to this algorithm, a sampling rate of about 0.5 Hz is appropriate. The median value of the three most recent sample points may be determined at step 605 to smooth the MV signal.

At step 615, the current, smoothed, MV value, MV(N), is compared to the previous MV value, MV(N−1). If the MV has decreased (MV(N) is less than MV(N−1)), then the onset of a provisionally-detected cycle is flagged at step 630, if a cycle onset has not already been flagged as determined at decision step 625. A duration counter is increased by one at step 635. The duration counter is used to track the duration of a continuous decrease in MV, which may indicate an episode of apnea. After the duration counter is increased at step 635, the next sample point from the minute volume input received at step 601 and smoothed at step 605, is compared to the previous MV value to determine if MV is still decreasing. If a subsequent MV sample point is found to be greater to the preceding MV sample at decision step 615, and the duration counter is greater than 0 as determined at step 620, a tolerance counter is increased by one at step 645 after verifying that a tolerance limit has not been exceeded at step 640. If the duration counter is not greater than 0 at step 620, then the onset of a potential apnea episode as evidenced by a declining MV, has not yet been detected and flagged. In this case, the method 600 continues to monitor the MV input until a decrease in MV is detected at step 615.

If the onset of a potential apnea episode has been flagged and the duration counter is greater than 0 at step 620, then some degree in fluctuation in MV may be tolerated in order to prevent noise artifacts from interfering with apnea detection. Thus, one or two increases in MV, for example, may be tolerated without terminating the apnea duration count. A tolerance limit, therefore, is predefined and may be programmable to a value preferably on the order of 1 or 2, which allows some fluctuation of the generally decreasing MV signal. If the tolerance counter is less than the tolerance limit at step 640, the tolerance counter is increased by one at step 645, and the duration counter is increased at step 635.

Once the tolerance limit is exceeded, MV is considered to be generally increasing again, signifying the end of the provisionally detected cycle. In order to verify that the decrease in MV was indeed associated with apnea, the duration counter is compared, at step 650, to a duration threshold that is pre-set according to a minimum apnea duration expected to occur with the disordered breathing pattern of interest. If the duration of the decreasing MV is less than the apnea duration threshold, an apnea episode is not verified. The cycle onset and tolerance and duration counters are reset at step 655, and the method 600 returns to step 601 to continue monitoring MV.

If the duration counter value is greater than the duration threshold at decision step 650, the decline in MV is provisionally determined to be associated with a valid apnea episode and the cycle onset and duration are stored in device memory at step 660. At step 665, the method 600 determines if this cycle is the first cycle detected. If so, the method 600 returns to step 601 to continue monitoring MV until another apnea cycle is provisionally detected. If this is not the first cycle detected, the cycle length is determined at step 670.

In this embodiment, the end point of a provisionally detected cycle is determined as the onset of a subsequently detected cycle. Therefore, the cycle length of the first cycle detected is determined as the difference between the onset of the first detected cycle and the onset of a second provisionally detected cycle. If the cycle length is within a predefined range associated with a disordered breathing cycle period, as determined at decision step 675, the preceding cycle is detected as a valid disordered breathing cycle at step 680. The currently detected cycle will be validated upon detecting the onset of the next suspected apnea cycle.

After detecting a valid cycle at step 680, a cycle counter may be increased, as described above in conjunction with step 320 of FIG. 2, so that consecutive, validated cycles may be counted in order to verify detection of a disordered breathing episode.

Figure 9:
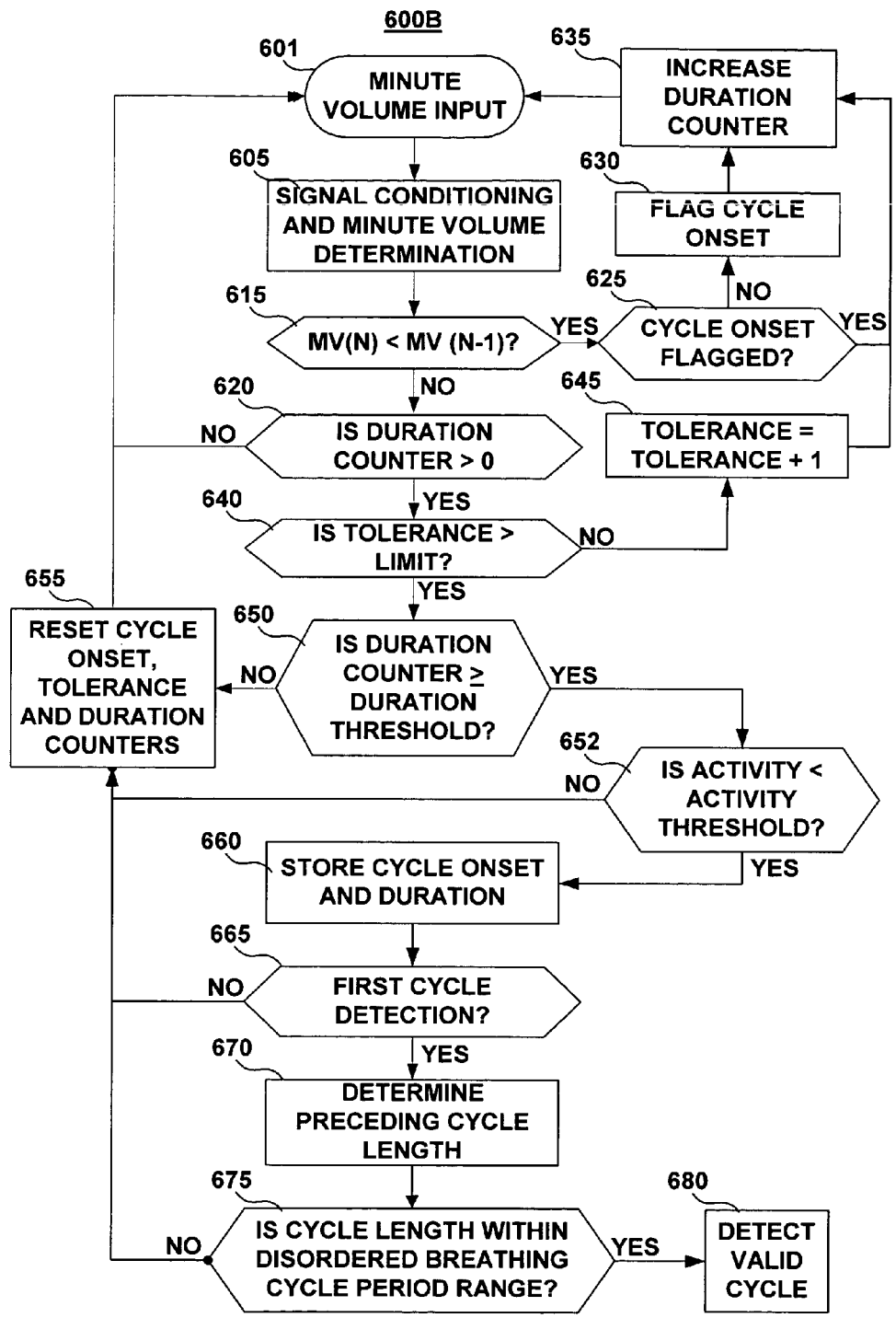
FIG. 9 is a flow chart summarizing the steps included in an alternative embodiment for monitoring oscillations of a physiological parameter due to disordered breathing which further includes an activity sensor cross-check.

FIG. 9 is a flow chart summarizing the steps included in an alternative embodiment for monitoring oscillations of a physiological parameter due to disordered breathing which further includes an activity sensor cross-check. When MV, or another physiological parameter, is monitored for the detection of sleep apnea, a sensor cross-check may be included which utilizes another sensor to verify that the patient is likely to be asleep, such as an activity sensor. Identically numbered steps in FIG. 9 correspond to those in FIG. 8. Decision step 652 is added after detecting a decreasing MV for a period of time that exceeds the apnea duration detection threshold at decision step 650. If a low level of activity is measured, as indicated by a sensed activity less than a predetermined activity threshold that corresponds to a resting level, the preliminary apnea detection is deemed correct. Method 600B will proceed to step 660 to test the periodicity of the cycle in order to validate the preliminary apnea cycle detection as described above.

If an activity level is measured which exceeds the predetermined activity threshold at step 652, the preliminary apnea detection is deemed unreliable and the method 600B resets the cycle onset and the tolerance and duration counters and returns to step 601 to continue monitoring the MV. A decreasing MV signal could be a normal response associated with a decreasing level of activity. This normal MV response to changing levels of activity should not be viewed as a detection of a possible apnea episode. Therefore, inclusion of a sensor cross-check by verifying the patient activity level is at a minimal value indicative of sleep can improve cycle detection specificity. The inventors believe that such additional rules will help provide accurate detection of the events correctly even during wake state (e.g., Cheyne-Stokes breathing events). Using cross-checking with an activity sensor signal is an optional precaution in case one wants to be conservative. If activity counts exceed its predetermined threshold—thus indicating a possible arousal from a sleeping state—then the algorithm can take that into account in determining the presence of apnea. In this regard one should note that activity sensor signals are typically filtered and averaged over a period of time.

Figure 10:
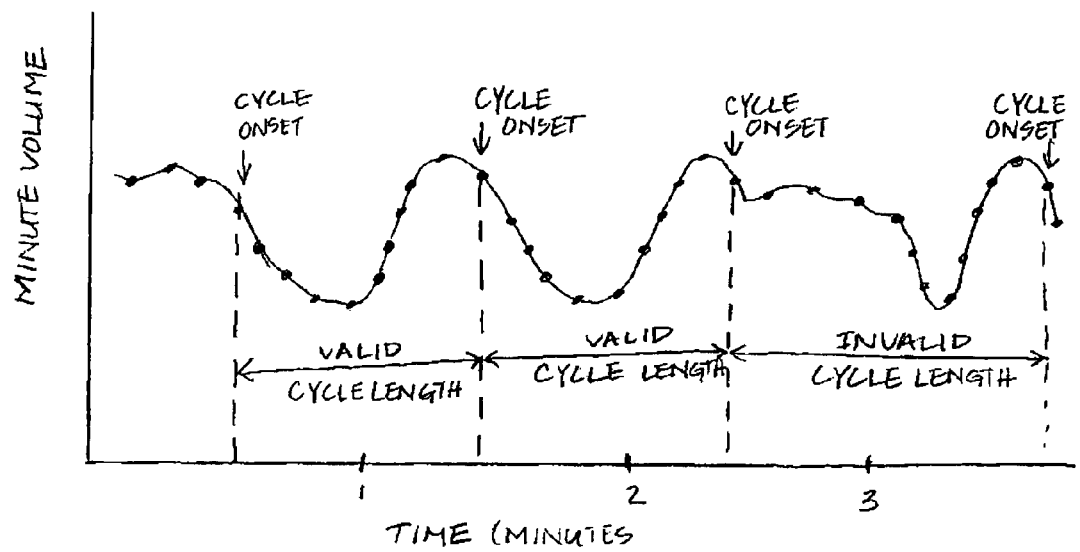
FIG. 10 is a graphical depiction of minute volume oscillations that may occur during disordered breathing and which may be used to detect apnea cycles according to the method of FIG. 8.

FIG. 10 is a graphical depiction of minute volume oscillations that may occur during disordered breathing and which may be used to detect apnea cycles according to the method of FIG. 8. A provisionally detected cycle onset is marked by a MV sample point that is less than the previous sample point. A provisionally detected cycle end is marked by the next provisionally detected cycle onset as described above in conjunction with FIG. 8. The difference between two cycle onsets is compared to a cycle length duration requirement to determine if the provisionally detected cycle is valid or invalid. Additional cycle validation criteria may be defined, such as maximum and minimum amplitude differences and so forth. In FIG. 10, two valid cycles are shown followed by a subsequent invalid cycle length.

Monitoring minute ventilation for detecting an apnea episode is advantageous in that respiration changes are measured directly. However, impedance sensing used for determining a minute volume can consume substantial device battery energy which is undesirable in devices expected to meet certain longevity needs, such as cardiac pacemakers. In pacemakers, implantable cardioverter defibrillators, and other types of cardiac monitoring or cardiac rhythm management devices, ongoing sensing of intrinsic cardiac events is typically standard device operation, except during certain device functions such as during pacing pulse or therapy delivery. In these types of devices, therefore, a sensed heart rate can be readily available based on sensed P-waves or R-waves and may advantageously be used for monitoring for cyclical changes that may be indicative of disordered breathing. However, the sensed intrinsic heart rate is not available during atrial-based cardiac pacing—but is available during ventricular-based pacing. To take advantage of the lower energy requirement of monitoring heart rate for sleep apnea detection and the more sensitive approach provided by MV monitoring while overcoming associated limitations as described above, one embodiment of the present invention includes a disordered breathing sensor switch.

Figure 11:
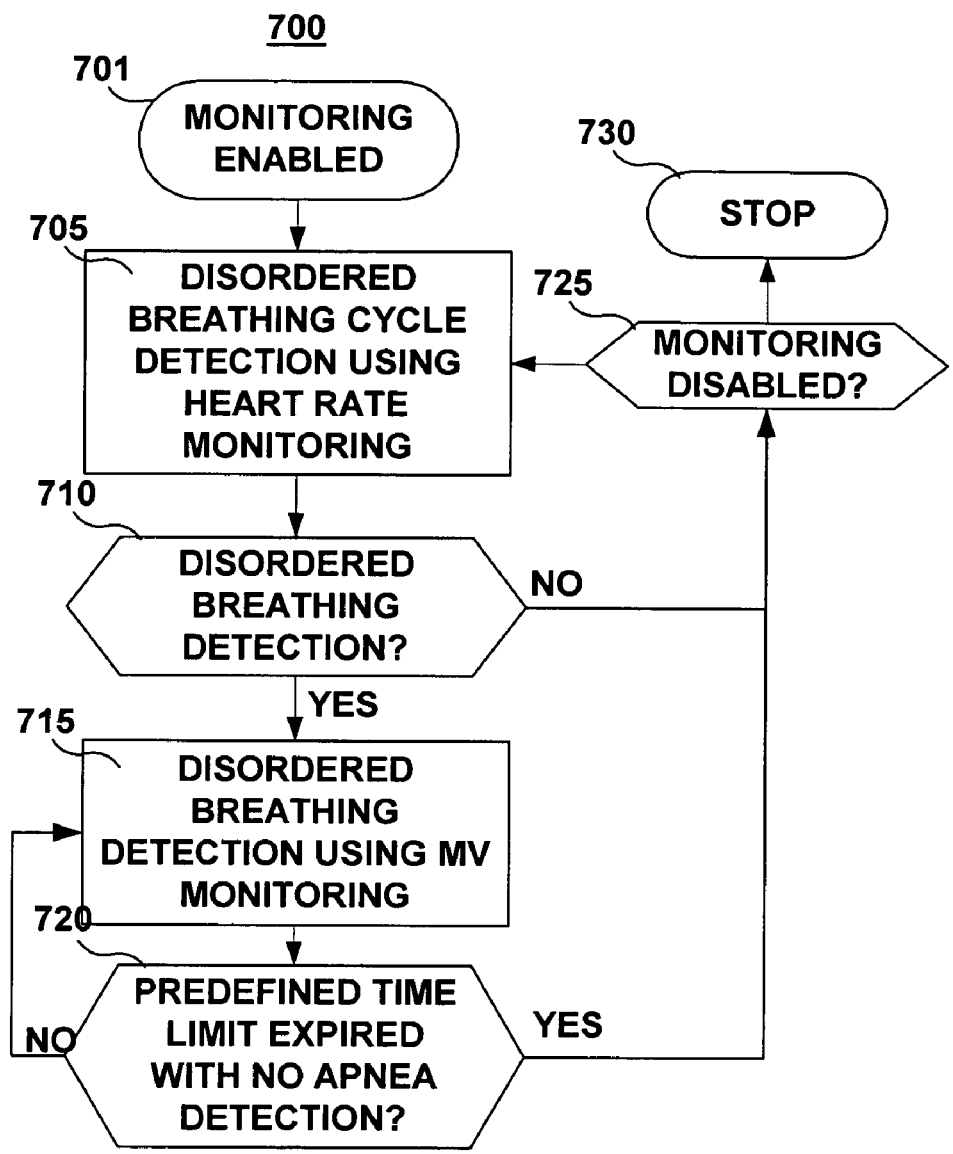
FIG. 11 is a flow chart summarizing the steps included in a method for switching between heart rate monitoring and MV monitoring employed by a disordered breathing monitoring algorithm in accordance with the present invention.

FIG. 11 is a flow chart summarizing the steps included in a method for switching between heart rate monitoring and MV monitoring employed by a disordered breathing monitoring algorithm in accordance with the present invention. Monitoring is enabled at step 701 by a real-time clock or timer, automatic triggering or patient triggering, as described previously. Initially, sleep apnea detection is performed using heart rate monitoring at step 705, preferably according to the method 500 described above in conjunction with FIG. 4. In no detected cycles are validated as apnea cycles or disordered breathing episodes are not detected at decision step 710, and monitoring is not yet disabled at determined at decision step 725, heart rate monitoring continues at step 705. If monitoring is disabled before an apnea episode is detected, the method 700 is terminated at step 730.

If an apnea episode is detected at decision step 710 based on heart rate monitoring and is verified as a valid apnea episode in accordance with the criteria defined for heart rate cycle period, cycle amplitude, number of cycles required and so forth, then sleep apnea detection is switched from heart rate monitoring to minute ventilation monitoring at step 715. MV monitoring is preferably performed according to the method described above in conjunction with FIG. 8 or 9.

If no apnea detections are made during a predefined period of time, for example on the order of 30 to 60 minutes, the MV sensor is disabled and sleep apnea detection is switched backed to heart rate monitoring at step 705, if monitoring has not yet been disabled as determined at decision step 725. If apnea episodes are detected (a negative result at decision step 720), MV monitoring continues at step 715. Thus, after an initial apnea episode detection using heart rate monitoring, which consumes relatively low battery energy, the algorithm 700 switches to MV monitoring, which consumes greater battery energy but is expected to be have greater specificity for apnea detection. After the initial detection, subsequent apnea events are highly likely, justifying the higher energy cost of enabling the impedance sensing.

Figure 12:
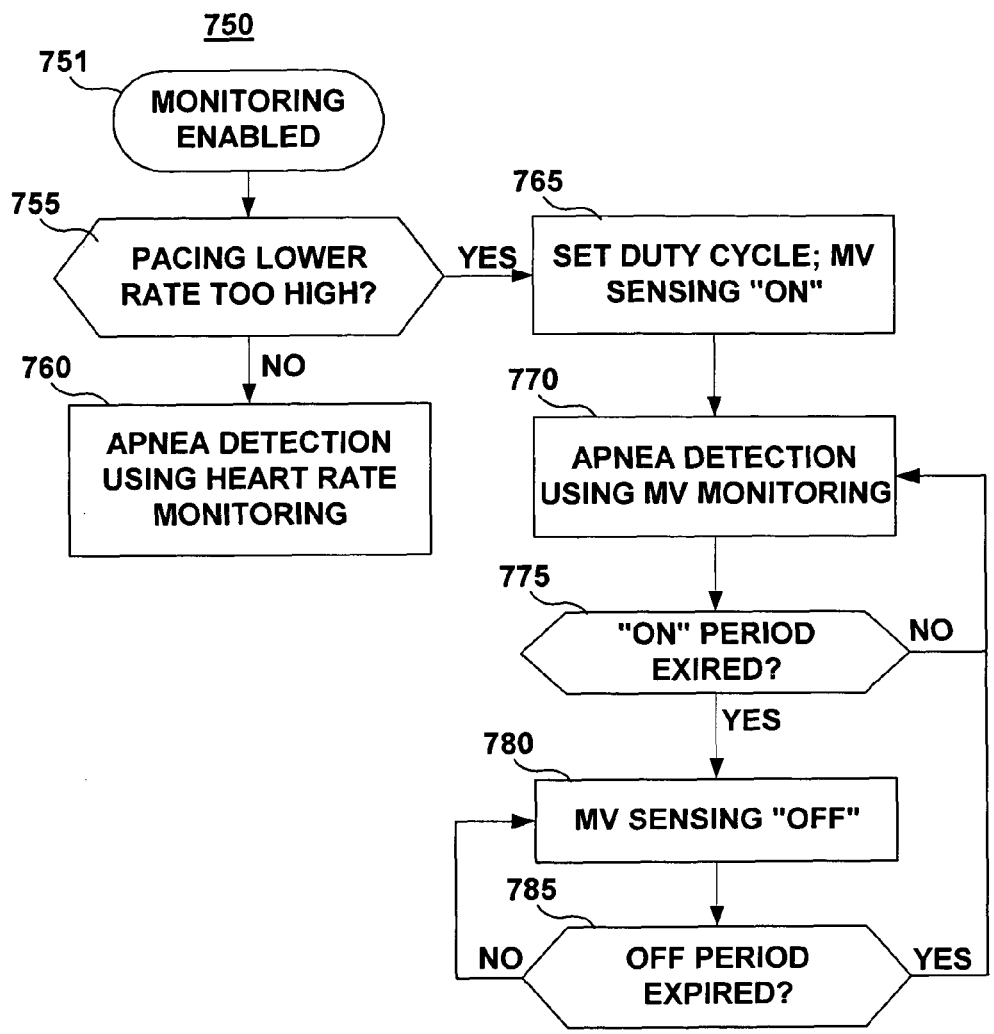
FIG. 12 is a flow chart summarizing the steps included in a disordered breathing detection method that includes a sensor switch and is appropriate for use in pacemaker-dependent persons.

As described above, a limitation of heart rate monitoring alone may exist when a patient being monitored for apnea is pacemaker dependent. FIG. 12 is a flow chart summarizing the steps included in a disordered breathing detection method that includes a sensor switch and is appropriate for use in pacemaker-dependent persons, or sick-sinus syndrome patients, as well as patients who are receiving "overdrive pacing therapy."

At step 751, monitoring is enabled as described previously. At decision step 755, the method 750 determines if the pacing lower rate is programmed too high to allow reliable sensing of heart rate oscillations associated with disordered breathing. For example, the heart rate during apnea may fall to rates on the order of 50 to 60 beats per minute, or lower. If the pacing lower rate is programmed to be 60 beats or higher, the lower intrinsic heart rate associated with apnea will not occur due to pacing, precluding accurate heart rate cycle detection. If the pacing lower rate is not determined to be too high to prevent intrinsic heart rate monitoring, then sleep apnea detection using heart rate monitoring is performed at step 760. Heart rate monitoring is preferably performed as described above in conjunction with FIG. 4.

If the lower rate is determined to be too high to allow reliable intrinsic heart rate monitoring at decision step 755, minute ventilation monitoring is enabled on a duty cycled basis to conserve battery energy but still provide reliable apnea detection during the duty period. At step 765, the MV monitoring duty cycle is set and MV sensing is turned "on." At step 770, sleep apnea detection is performed using MV monitoring, preferably according to the methods described above in conjunction with FIGS. 8 or 9. MV monitoring continues until the duty cycle "on" period expires as determined at decision step 775. Once the duty cycle "on" period has expired, MV sensing is turned "off" at step 780 and remains off until the duty cycle "off" period has expired as determined at decision step 785. After the "off" period is expired, the MV monitoring is restarted by returning to step 770. The duty cycle periods may be programmable values and may be on the order of 1 night on and several days off. For example, if a monitoring period of one week has been enabled, MV monitoring may be cycled to occur two nights and off two nights. In a similar manner, a device implementing the methods of the present invention may operate only for a limited amount of time per day. For example, an implantable medical device operating for approximately six hours per day (whether by remote activation, using a 24 hour timer, or triggered from a sensor indicating a patient has begun sleeping, and the like) can be expected to have approximately a four-fold increase in system longevity. Thus, for a patient having an average AHI over some predetermined, or agreed upon, threshold a single implantable medical device providing detection of apneic events and therapy therefor (e.g., NOP) that also has a reasonably long service life is provided.

Figure 13:
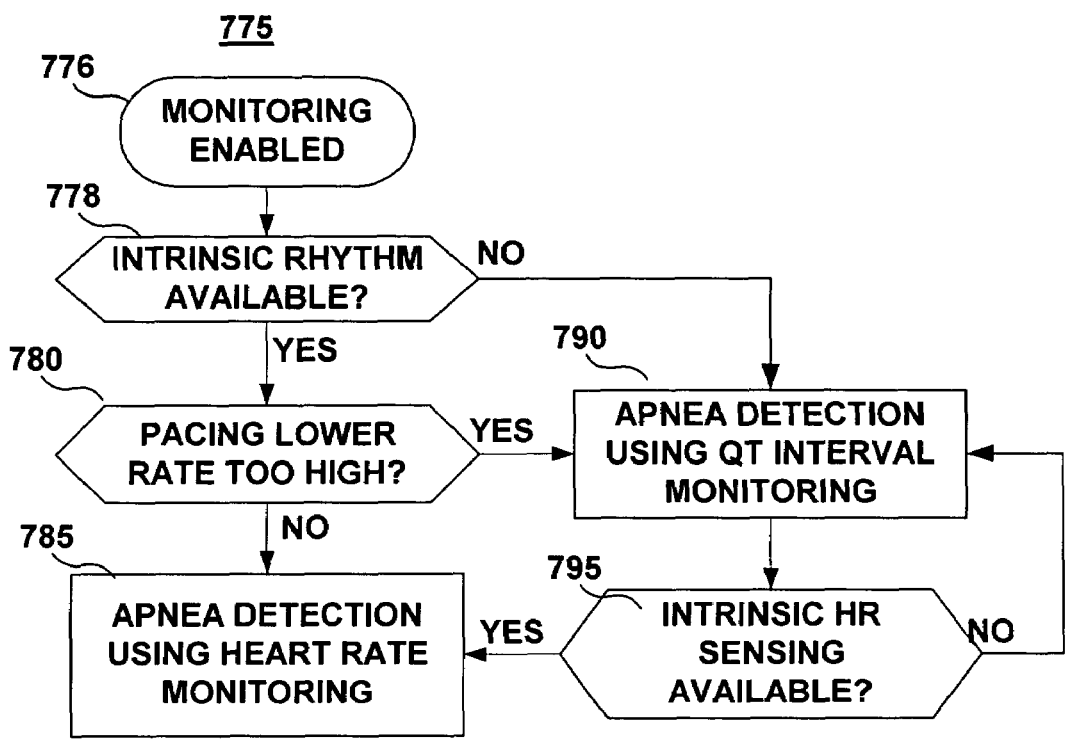
FIG. 13 is a flow chart depicting an alternative disordered breathing monitoring method appropriate for use in pacemaker-dependent persons.

FIG. 13 is a flow chart depicting an alternative disordered breathing monitoring method appropriate for use in pacemaker-dependent persons. This method 775 may be used in particular if HR sensing based on EGM or ECG signal is available but not MV sensing. At step 776, monitoring is enabled, and at step 778 method 775 determines if intrinsic rhythm sensing is available. If the patient is being paced a substantial amount of time, the intrinsic heart rate is not available for detecting heart rate cycles associated with apnea-hyperpnea cycles. If the intrinsic rate is available, the method 775 checks the pacing lower rate to ensure that the lower rate is not programmed too high to preclude accurate heart rate cycle detection. If the pacing lower rate is not too high, apnea detection may be performed at step 785 by monitoring heart rate in accordance with the methods described above.

If the intrinsic rhythm sensing is not available or the pacing lower rate is too high, then apnea detection is performed based on monitoring changes in the Q-T interval. Q-T intervals may be detected by analyzing EGM segments or by sensing R-waves and T-waves and determining the time interval between sensed R-waves and T-waves. A method for monitoring Q-T interval changes is generally disclosed in U.S. Pat. No. 6,161,041 issued to Stoop, et al., incorporated herein by reference in its entirety. As noted previously, Q-T interval variation during apnea-hyperpnea cycles has been found to follow a similar pattern as the bradycardia-tachycardia cycles associated with apnea-hypopnea cycles. Therefore, monitoring of Q-T interval variations for detecting Q-T cycle changes associated with apnea may be performed according to the method 500 as generally described above in conjunction with FIG. 4. If at any time during Q-T interval monitoring, intrinsic rhythm sensing becomes available again, as determined at decision step 795, disordered breathing monitoring may convert to apnea detection based on heart rate monitoring at step 785.

Thus a method and apparatus have been described which enable disordered breathing monitoring to be performed based on detection of cyclic oscillations of physiological parameters that are correlated to apnea-hypopnea alternation. A number of disordered breathing metrics may be determined from detection of apnea-related cycles to provide a physician with valuable information for screening and diagnosing patients with disordered breathing conditions. Trends in disordered breathing metrics may be used for prognostic purposes, such as monitoring the incidence of Cheyne-Stokes breathing in patients suffering from congestive heart failure. Trends in disordered breathing metrics may also be used for evaluating a prescribed therapy. While specific embodiments have been described herein, it is recognized that numerous variations are possible for monitoring for disordered breathing patterns based on cyclical changes in one or more sensed physiological parameter. Thus, the disclosed embodiments are intended to be exemplary and not as limiting with regard to the following claims.

We claim:

1. A method of detecting disordered breathing in an implantable medical device in a patient, comprising:
   monitoring a physiologic characteristic of a patient that is a direct indicator of heart rate with at least one implantable sensor that provides an output signal indicative of the heart rate;
   identifying a cyclical variation of the heart rate, the cyclical variation comprising a first period corresponding to a first heart rate alternating with a second period corresponding to a second heart rate greater than the first heart rate;
   comparing said cyclical variation to threshold criteria indicative of a sleep disordered breathing event; and
   declaring the presence of the disordered breathing episode in the event that there is a positive correlation between the comparison of the cyclical variation and the threshold.

2. A method according to claim 1, wherein the at least one sensor is an electrogram circuit and said electrogram circuit further comprises at least a pair of electrodes electrically coupled to the implantable medical device.

3. A method according to claim 2, further comprising an impedance sensor coupled to a sensing circuit of the implantable medical device.

4. A method according to claim 1, wherein the at least one sensor is an impedance sensor.

5. A method according to claim 1, wherein said at least one sensor is a QT interval measurement means.

6. A method according to claim 5, further comprising withholding a declaration of the presence of the disordered breathing event until a preset number of cardiac cycles have occurred.

7. A method according to claim 1, wherein a predetermined sensing period is defined and the aggregate number of declared disordered breathing events is divided by the sensing period so that an index value is calculated for said sensing period.

8. A method according to claim 1, further comprising providing an anti-disordered breathing electrical stimulation therapy to a portion of tissue of said patient.

9. The method of claim 1 wherein identifying a cyclical variation of the heart rate comprises:
   determining a mean heart rate;

setting an upper rate threshold and a lower rate threshold in response to the determined mean heart rate;

detecting a first crossing of the lower rate threshold;

detecting a first crossing in an upper direction of the upper rate threshold subsequent to the first crossing of the lower rate threshold;

detecting a second crossing in a downward direction of the upper rate threshold subsequent to the first upper rate threshold crossing;

detecting a second crossing of the lower rate threshold subsequent to the second upper rate threshold crossing; and identifying the cyclical variation in heart rate in response to the detected second crossing.

10. The method of claim 9 wherein detecting the cyclical variation in heart rate further comprises:

setting a cycle onset time in response to the first crossing of the lower rate threshold, setting a cycle end time in response to the second crossing of the lower rate threshold; and comparing the difference between the cycle onset time and cycle end time to a disordered breathing cycle length threshold.

11. The method of claim 10 further comprising:

detecting if more than two consecutive crossings of one of the upper and lower rate thresholds occurs without an intervening crossing of the other of the upper and lower rate threshold;

detecting an invalid cyclical variation in heart rate for detecting disordered breathing in response to detecting the more than two consecutive crossings.

12. An implantable device for detecting, and optionally, providing a therapy for disordered breathing, comprising:

means for sensing a physiologic parameter that is a direct indicator of heart rate with an implantable sensor;

means for detecting a cyclical variation in the sensed physiologic parameter of a patient, wherein said cyclical variation of the heart rate occurs during an episode of disordered breathing, the cyclical variation comprising a first period corresponding to a first heart rate alternating with a second period corresponding to a second heart rate greater than the first heart rate;

means for comparing said cyclical variation to a threshold criteria; and means for setting a disordered-breathing-detected marker in the event that said cyclical variation exceeds the threshold criteria.

13. A device according to claim 12, wherein said means for detecting includes means for providing QT interval monitoring.

14. A device according to claim 12, wherein said means for detecting further comprise an EGM circuit coupled to at least one electrode.

15. A device according to claim 12, further comprising means for providing an electrical stimulation therapy intended to abate the disordered breathing episode.

16. A device according to claim 15, further comprising means for storing data related to each of a plurality of detected episodes of disordered breathing.

17. A device according to claim 16, further comprising means for calculating a disordered breathing index based at least in part upon the stored data.

18. A device according to claim 12, wherein said means for detecting comprises at least two physiologic sensors and further comprising means for comparing an output signal set from said sensors to confirm or deny the presence of an episode of disordered breathing and/or for switching from a one of said at least two physiologic sensor to another of said at least two physiologic sensors.

* * * * *